(12) United States Patent
Oohira et al.

(10) Patent No.: US 7,419,476 B2
(45) Date of Patent: Sep. 2, 2008

(54) PRESSURE-SENSITIVE ADHESIVE COMPONENT FOR ANKLE AND USE THEREOF

(75) Inventors: Osamu Oohira, Osaka (JP); Yoshitada Morikawa, Osaka (JP); Kotaro Shimobayashi, Osaka (JP)

(73) Assignee: Nitto Denko Corporation, Osaka (JP)

( * ) Notice: Subject to any disclaimer, the term of this patent is extended or adjusted under 35 U.S.C. 154(b) by 303 days.

(21) Appl. No.: 10/865,751

(22) Filed: Jun. 14, 2004

(65) Prior Publication Data
US 2005/0015037 A1 Jan. 20, 2005

(30) Foreign Application Priority Data

| Jun. 13, 2003 | (JP) | ............................. 2003-169111 |
| Jun. 25, 2003 | (JP) | ............................. 2003-180504 |

(51) Int. Cl.
*A61F 13/06* (2006.01)
(52) U.S. Cl. .............................. 602/65; 602/23; 602/27; 602/60
(58) Field of Classification Search ...................... 602/1, 602/62–66, 44, 48, 52, 45, 41, 3, 6, 19–23, 602/26, 27, 53, 75, 76, 904, 903; 128/892
See application file for complete search history.

(56) References Cited

U.S. PATENT DOCUMENTS

| 3,312,219 A | * | 4/1967 | Peckham ..................... 602/65 |
| 3,357,425 A | * | 12/1967 | Morgan ........................ 602/41 |
| 3,508,544 A | * | 4/1970 | Moore et al. ................. 128/892 |
| 4,133,311 A | * | 1/1979 | Karczewski .................. 602/65 |
| 4,345,590 A | * | 8/1982 | Nakajima ..................... 602/65 |
| 4,433,682 A | * | 2/1984 | Badra .......................... 128/892 |
| 4,875,476 A | * | 10/1989 | Garcia ......................... 602/65 |
| 5,897,518 A | * | 4/1999 | Shaw .......................... 602/65 |
| 2004/0158187 A1 | * | 8/2004 | Huppert ...................... 602/65 |

FOREIGN PATENT DOCUMENTS

| DE | 196 46 740 A1 | 5/1998 |
| EP | 0 621 023 A2 | 10/1994 |
| JP | 10-24055 A | 1/1998 |
| JP | 10-248865 A | 9/1998 |

* cited by examiner

*Primary Examiner*—Justine R. Yu
*Assistant Examiner*—Shumaya Ali
(74) *Attorney, Agent, or Firm*—Sughrue Mion, Pllc.

(57) ABSTRACT

To provide a pressure-sensitive adhesive component that can be quickly and easily used to fix an ankle joint by persons having no expert knowledge on taping without causing problems such as difficulty in wearing shoes due to thickening upon application of the tape, a pressure-sensitive adhesive component includes a bottom portion; a first tape-shaped body; and a second tape-shaped body, wherein a cut is provided between the first and second tape-shaped bodies running in a longitudinal direction, the first tape-shaped body including a first front tape body and a first rear tape body, and the second tape-shaped body including a second front tape body and a second rear tape body, and wherein a ratio of a width of the front tape body to a width of the rear tape body is within the range of 5:5 to 5:3.

20 Claims, 14 Drawing Sheets

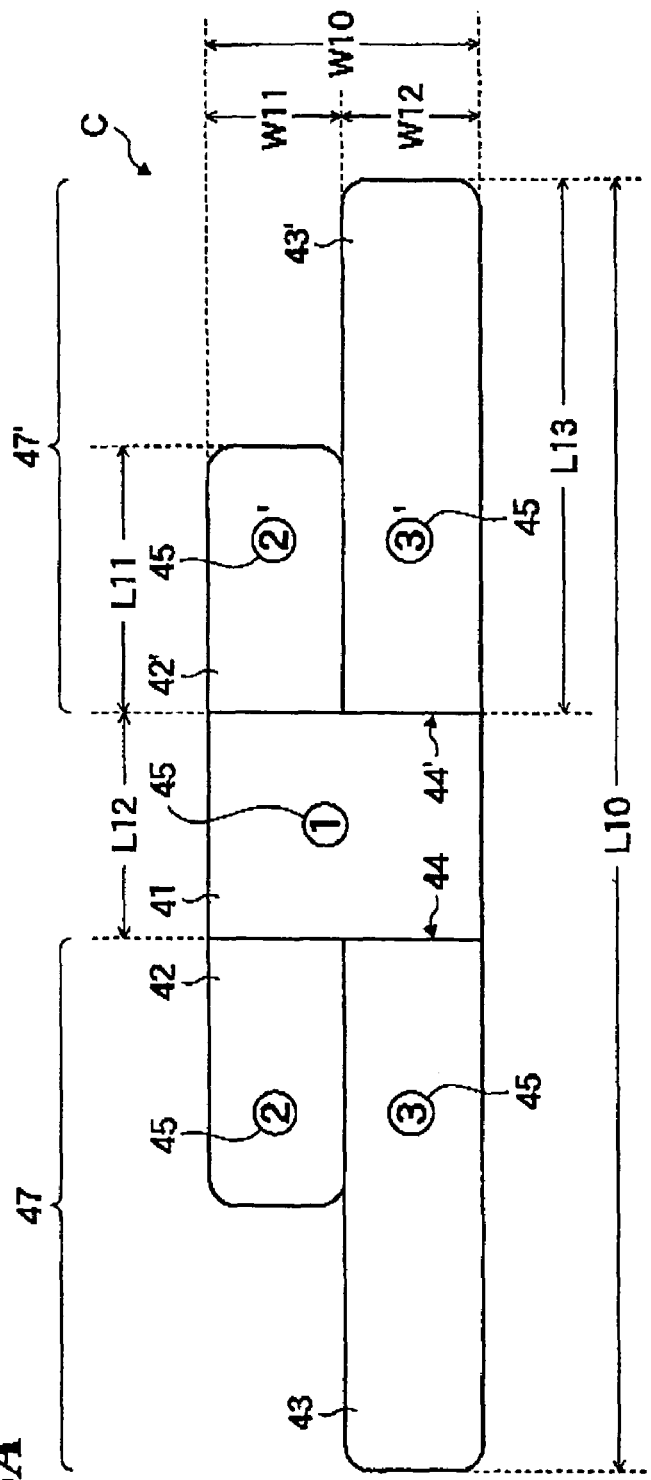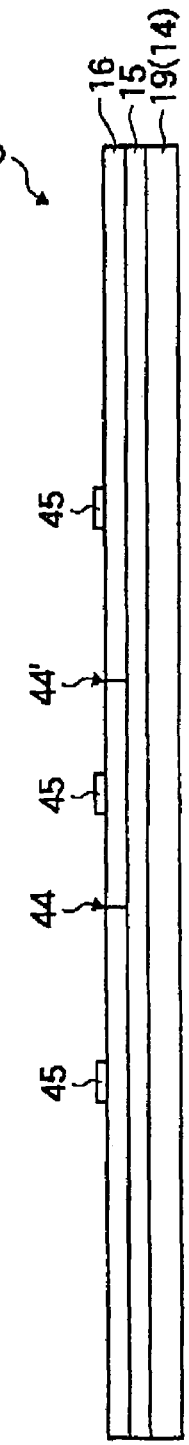
FIG.8A
FIG.8B

PRESSURE-SENSITIVE ADHESIVE COMPONENT FOR ANKLE AND USE THEREOF

BACKGROUND OF THE INVENTION

1. Field of the Invention

The present invention relates to a pressure-sensitive adhesive component for an ankle and to a method for using it. More particularly, the present invention relates to a pressure-sensitive adhesive component used for fixing ankle joints and the like in the fields of medicine, sports, chiropractic and so on and to a method for using such a pressure-sensitive adhesive component.

2. Description of Related Art

An ankle is a portion of a body that supports the body and thus is loaded with the body weight and that tends to suffer a sprained ankle in porting, daily life and so on. Since the ankle is closely involved in walking, a pain in the ankle makes daily motion difficult. Accordingly, there has been a keen desire for a countermeasure to alleviate the pain that occurs in the ankle. For example, a treatment to fix the ankle joint and the like has been performed.

A method for fixing the ankle joint and the like without requiring expert knowledge includes a method of attaching a supporter around an ankle disclosed in Japanese Patent Application Laid-Open No. 10-24055. The supporter has a shin pad formed to have a large thickness and use of the pad results in thickening of the ankle so that one cannot wear shoes or the like when he or she has attached the shin pad around the ankle. This is inconvenient to daily life motions. Further, a supporter for a foot joint made of an elastic tape-shaped body, including an anchor strap that winds up around an ankle, a figure eight strap that winds up around a dorsum of the foot and a sole of the foot in the form of a figure eight (8), and a stirrup strap that winds up around the foot from a medial malleolus to a lateral malleolus through the sole is disclosed in Japanese Patent Application Laid-Open No. 10-248865. The supporter loosens with a lapse of time, thus failing to fix the ankle joint and the like sufficiently.

Fixing or otherwise restricting the movement of an ankle joint by using a pressure-sensitive adhesive tape in order to alleviate the pain of the ankle (taping) is a conventional treatment performed in the fields of sports and medicine. Appropriate taping can sufficiently fix the ankle to alleviate the pain of the ankle and will not reduce the ability of the ankle and the like to move. However, the conventional treatment has the defect that appropriate taping cannot be readily performed since expert knowledge is required for performing such taping. Also, it has the problem that taping by spirally winding a pressure-sensitive adhesive tape around an ankle in an overlapping manner tends to cause local circulation disturbance and nervous disturbance due to over constriction.

SUMMARY OF THE INVENTION

The present invention has been made under the above-mentioned circumstances and an object of the present invention is to provide a pressure-sensitive adhesive component for an ankle portion with which a person having no expert knowledge on taping can fix the ankle quickly and easily and which causes no problems such as failure to wear shoes due to the attachment of a fixing member or the like and thickening of the ankle an a result of application of the tape. Another object of the present invention is to provide a method for fixing an ankle joint and the like by using the pressure-sensitive adhesive opponent for an ankle portion.

The present invention provides a pressure-sensitive adhesive component for an ankle comprising an H-shaped pressure-sensitive adhesive component including:

a bottom portion;

a first tape-shaped body provided on the bottom portion; and a second tape-shaped body provided on the bottom portion, wherein a cut is prodded between the first and second tape-shard bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and wherein a first ratio of a width of the first front tape body to a width of the first rear tape body and a second ratio of a width of the second front tape to a width of the second rear tape body are independently within the range of 5:5 to 5:3.

According to one aspect, the pressure-sensitive adhesive component for an ankle of the present invention includes an H-shaped pressure-sensitive adhesive component including: a bottom portion; a first tape-shaped body provided on the bottom portion; and a second tape-shaped body provided on the bottom portion, wherein one edge of the bottom portion is concave, wherein a cut in provided between the first and second tape-shaped bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and wherein a first ratio of a width of the first front tape body to a width of the first rear tape body positioned on the side of the concave edge and a second ratio of a width of the second nd front tape body to a width of the second rear tape body positioned on the side of the concave edge are independently within the range of 5:5 to 5:3.

Here, the H-shaped pressure-sensitive adhesive component may have a length of 300 mm to 600 mm mod the first and second tape-shaped bodies may independently have a width of 50 mm to 150 mm.

According to another aspect, the pressure-sensitive adhesive component for an ankle of the present invention includes a modified H-shaped pressure-sensitive adhesive component, including a rectangular bottom portion; a first rear tape body and a front tape body extending from one edge of the bottom portion having respective axes parallel to each other; and a second rear tape body and a second front tape body extending from an opposite edge of the bottom portion having respective axes parallel to each other, wherein the first and second rear tape bodies have lengths shorter than those of the first and second front tape bodies.

Here, the pressure-sensitive adhesive component may have a length from an edge of the first front tape body to an end of the second front tape body of 400 mm to 650 mm, and the first and second tape-shaped body may independently have a width of 50 mm to 150 mm.

Further, the first and second front tape bodies nay independently have a length of 200 mm to 270 mm.

Still further, the first and second rear tape bodies may independently have a length of 80 mm to 150 mm.

In the present invention, it is preferable that head portions of the first rear tape body, the first front tape body, the second rear tape body, and the second front tape body arm each tongue-shaped.

It is preferable that the pressure-sensitive adhesive component for an ankle includes a Substrate and a pressure-sensitive adhesive layer and the pressure-sensitive adhesive layer is covered with a release liner.

Sere, the substrate may be made of a high twist fabric, an elastic knitted fabric or an elastic woven fabric.

The pressure-sensitive adhesive layer may be made of an acrylic-based pressure-sensitive adhesive or a gel-based pressure-sensitive adhesive.

The pressure-sensitive adhesive component for an ankle of the present invention may further include an auxiliary pressure-sensitive adhesive component in a rectangular form having a shorter side and a longer side and a curved corner, as an independent element.

In the present invention, the H-shaped pressure-sensitive adhesive component or the modified H-shaped pressure-sensitive adhesive component may include a release liner that covers the pressure-sensitive adhesive layer and is separated by a back slit and has indicated thereon a character or an image thereon Here, one can recognize an order from the character or image put on the release liners separated by the back splits.

The taping method by using the H-shaped pressure-sensitive adhesive component of the present invention includes: removing a release liner on a bottom portion; placing a heal such that an edge of the heel is in line with a concave edge of the bottom portion; removing a release liner on a front tape portion to be applied to an outer wide of the ankle portion and applying the front tape portion with holding a head portion of a front tape body while expanding the front tape portion so as to cover a medial malleolus of the ankle portion from a heal toward a knee joint; removing a release liner on a front tape head portion and applying the front tape head portion; removing a release liner on a front tape portion to be applied to an inner side of the ankle portion and applying the front tape portion while drawing up the front tape portion just above and expanding; removing a release liner on a front tape head portion and applying the front tape head portion; removing a release liner on a rear tape portion positioned on an outer side of the ankle portion and applying the rear tape portion by holding a head portion of a rear tape body so as to pass along the back side of the ankle portion and cover over the medial malleolus while expanding the rear tape portion; removing a release liner of a rear tape head portion and applying the rear tape head portion; removing a release liner on a rear tape portion positioned on the inner side of the ankle portion and applying the rear tape portion by holding a head portion of a rear tape body and while expanding the rear tape portion so as to pass along the back side of the ankle portion and cover over the lateral malleolus; and removing a release liner of a rear tape head portion and applying the rear tape head portion.

Here, one edge of the auxiliary pressure-sensitive adhesive may be applied onto the rear tape portion so as to cover the lateral malleolus of the ankle portion in an overlapping manner and then the other edge of the auxiliary pressure-sensitive adhesive component may be applied to onto the other rear tape portion so as to cover the medial malleolus of the ankle portion in an overlapping manner.

The taping method by using the modified H-shaped pressure-sensitive adhesive component includes removing a release liner of a bottom portion and placing a heel sole on the bottom portion such that a rear tape body covers a surface of malleolus when elevated vertically; removing a release liner of one of the rear tape bodies and applying the rear tape body by holding a head portion of the rear tape body to lift the rear tape body vertically while expanding the rear tape body so as to cover the lateral malleolus of the ankle portion; removing a release liner of the other rear tape body to be applied to an inner side of the ankle portion and applying the rear tape body while lifting the rear tape body vertically to expand the rear tape body so as to cover an inner side of the ankle portion; removing a release liner of one of the front tape bodies positioned on an outer side of the ankle portion and applying the front tape body while holding a head portion of the front tape body to expand the front tape body so as to paws along an entire loop from above the dorsum of foot and the ankle portion and cover over the lateral malleolus and further pass Achilles' tendon on the back side of the ankle to the lateral malleolus; and removing a release liner of the other front tape body positioned on the inner side of the ankle portion and applying the front tape body while holding a head portion of the front tape body to expand the front tape body so as to pass along an entire loop including crossing at the ankle portion above the dorsum of foot to cover over the lateral malleolus, passing the Achilles' tendon to reach the medial malleolus.

In the present invention, it is preferable that the head portion is applied after relaxation of elongation of the head portion.

BRIEF DESCRIPTION OF THE DRAWINGS

FIG. 8A is a plan view showing a pressure-sensitive adhesive component for an ankle C according to a third embodiment of the present invention;

FIG. 8B is a front view of the pressure-sensitive adhesive component for an ankle C shown in FIG. 8A;

DETAILED DESCRIPTION

Figure 1A:
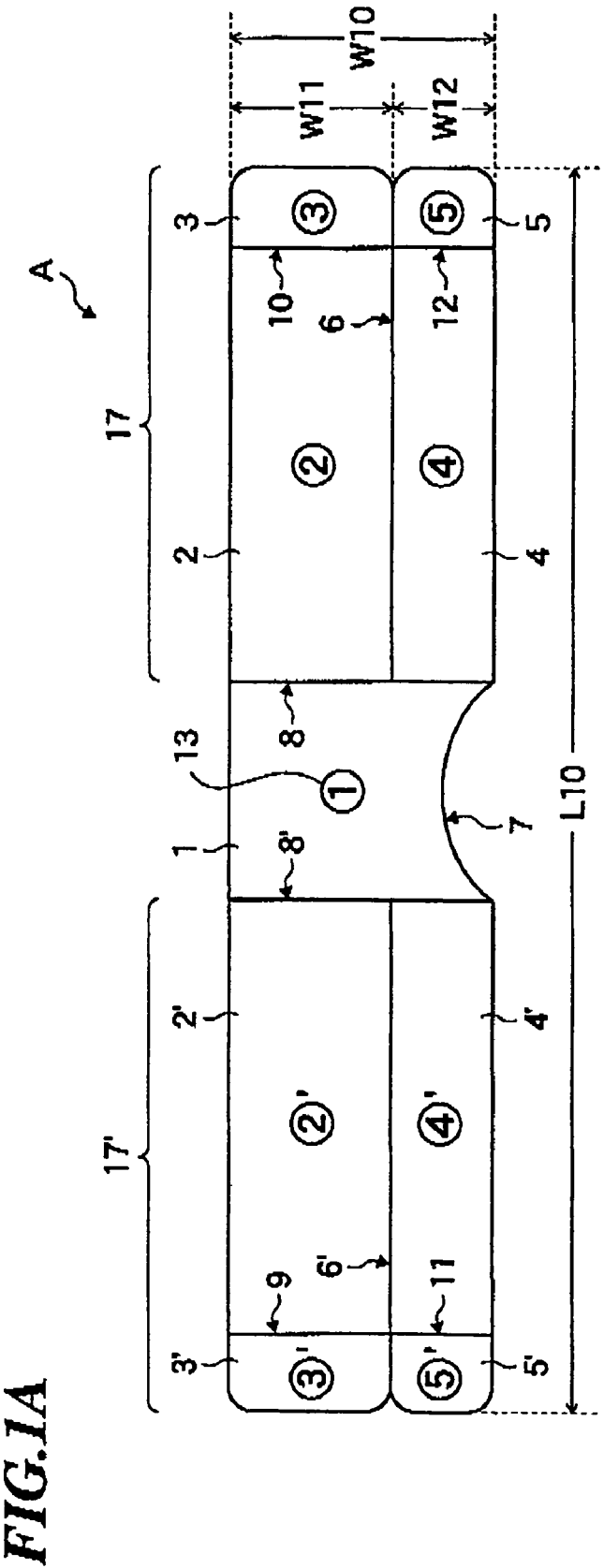
FIG. 1A is a plan view showing a pressure-sensitive adhesive component for an ankle according to a first embodiment of the present invention.

The pressure-sensitive adhesive component for ankle of the present invention is an H-shaped pressure-sensitive adhesive component that includes a bottom portion, a first tape-shaped body and a second tape-shaped body, with the first and second tape-shaped each being constituted by a front tape portion and a rear tape portion. The bottom portion may be rectangular or may form a concave edge on one end.

Hereinafter, the present invention will be described in detail by embodiments with reference to the attached drawings. The same or like constituent elements are indicated by the same reference numerals and detailed explanation thereof is omitted.

Figure 1B:
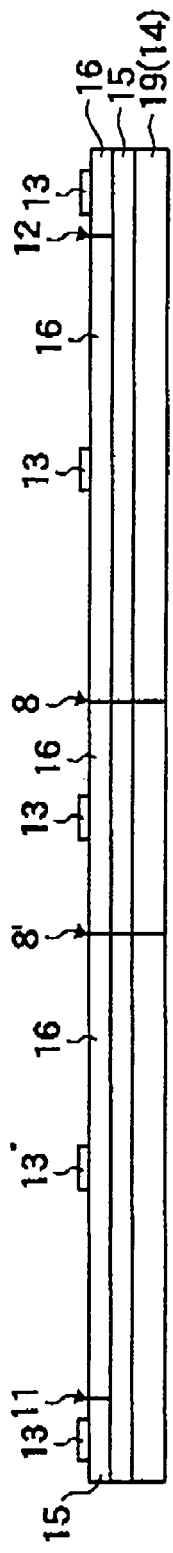
FIG. 1B is a front view of the pressure-sensitive adhesive component for an ankle shown in FIG. 1A.

FIG. 1A is a plan view showing a pressure-sensitive adhesive component for an ankle according to a first embodiment of the present invention and FIG. 1B is a front view of the pressure-sensitive adhesive component for an ankle shown in FIG. 1A. Here, explanation will be made on a pressure-sensitive adhesive component for an ankle including an H-shaped pressure-sensitive adhesive component.

In FIG. 1A, an H-shaped pressure-sensitive adhesive component A has a substantially rectangular contour and includes a bottom portion 1 to be applied to a heel sole of the foot substantially in the center thereof and tape-shaped bodies 17 and 17' to be applied to side and back surfaces, respectively, of the ankle on right-hand and left-hand sides, respectively, of the bottom portion 1. The right and left tape-shaped bodies 17 and 17' are formed with cuts 6 and 6', respectively, running from respective shorter edges of the substantially rectangular pressure-sensitive adhesive component A (hereinafter, referred to "shorter rectangular edge") to reach the bottom portion; thus the right tape-shaped body is divided into a first front tape body and a first rear tape body, and the left tape-shaped body in divided into a second front tape body and a second rear tape body. The first front tape body has a front tape portion 2 and a front taps head portion 3 and the first rear tape body has a rear tape portion 4 and a rear tape head portion 5. The second front tape body has a front tape portion 2' and a front tape head portion 3' and the second rear tape body has a rear tape portion 4' and a rear tap head portion 5'. The respective head portions of the front body and rear tape body, i.e., the front tape head portion 3 and 3, and the rear tape head portion 5 and 5' are tongue-shaped. The term "tongue-shaped" as used herein means a shape like a rectangle with the corner portions thereof being cut off, including for example, shapes similar to curves, such ax polygonal, semicircular, elliptical, R-shaped and the like curves. If the front tape head portions and rear tape head portions are rectangles with corners as they are the front and rear tape bodies tend to be peeled off when they are applied on the already applied pressure-sensitive adhesive component (including the own back sides of them) whereas forming head portions into a tongue shape makes them difficult to be peeled off when applied in an overlapping manner one on another. The positions of the cuts 6 and 6' are preferably such that the ratio of the width of the front tape portion 2 (W11) and the width of the rear tape portion 4 (W12) is within the range of, for example, W11:W12=5:5 to 5:3. In addition, the position of the left cut 6' and that of the right cut 6 maybe the same or different but it is preferred that the positions of both are preferably within the above-mentioned range.

The bottom portion 1 has a concave edge 7 on one side edge on the side of the rear tape portions. The shape of the concave edge 7 is preferably such that it allows the and of the heel of foot to run off from the bottom portion 1 to some extent.

Although the layer structure of the pressure-sensitive adhesive component for an ankle of the present invention will be described in detail later on, here a brief explanation is made. To prevent attachment of dust and the like to the pressure-sensitive adhesive layer to protect it until use, it is preferable that a release liner is laminated on the pressure-sensitive adhesive layer. It is also preferable that the release liner is provided with a back split at several positions. For example, back splits are provided at a boundary portion 9 between the bottom portion I and the first front tape portion 2 and rear tape portion 4 and similarly at the left-hand side boundary portion 8'. The back splits are also provided at a boundary portion 10 between the first front-tape portion 2 and the front tape head portion 3 and similarly at the boundary portion 9 between the second front tape portion 2' and the front tape head portion 3'. Further, back splits are provided at the boundary portion 12 between the first rear tape portion 4 and the rear tape head portion 5 and similarly at the boundary portion 11 between the second rear tape portion 4, and the rear tape head portion 5'. In the case of the H-shaped pressure-sensitive adhesive component shown in FIG. 1, numeric symbols (such as ①, ②, and ②') are put as by printing on the release liner of each part separated by the back split. Although what is put is not limited to numerical symbols, it is preferable that images such as characters (including numerical symbols) showing the order of taping and illustrations are indicated by any appropriate method.

The substantially rectangular H-shaped pressure-sensitive adhesive component shown in FIG. 1 has a shorter rectangular edge length (W10) of preferably 50 mm to 150 mm and a longer rectangular edge length (L10) of preferably 300 mm to 600 mm. It is preferable that the pressure-sensitive adhesive component is designed appropriately within such a range in consideration of the body type, foot type and so forth.

Further, the each out 6,6' has a length of preferably 150 mm to 250 mm. It is preferable that the length and a size and a shape of the bottom portion are designed appropriately within such a range in consideration of the body type, foot type and so forth.

Figure 2:
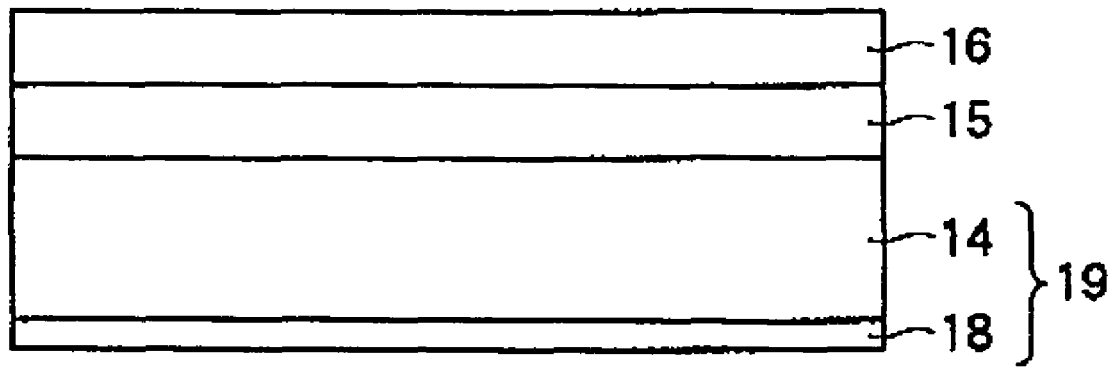
FIG. 2 is a cross-sectional view illustrating a layer structure of the pressure-sensitive adhesive component for an ankle according to the present invention.

FIG. 1B shows an example of the layer structure of the pressure-sensitive adhesive component for an ankle A. In FIG. 1B, the pressure-sensitive adhesive component for an ankle includes a support 19, a pressure-sensitive adhesive layer 15 and a release liner 16. Here, the support 19 is constituted by a substrate 14 only. However, the support 19 may be a laminate of the substrate 14 and another layer 18 provided thereon as shown in FIG. 2. The type and the like of another layer 18 may be selected appropriately an necessary. Although the release liner 16 may be omitted, it is preferable that the release liner 16 in laminated on the pressure-sensitive adhesive layer 15 in order to prevent the pressure-sensitive adhesive layer 15 from being contaminated with dust and dirt and protect adhesive power until use.

In FIG. 1B, the release liner 16 is provided with back splits at the boundary portions (8, 8', 11, 12) of each part and each release liner that covers each part is formed with a printed portion 13 where a numerical symbol (such a ① or ②) is printed.

The release liner may be one that man be used pressure-sensitive adhesive tapes generally applied to the skin. Specifically, use can be made of high-quality paper, glassine paper, parchment paper and the like coated thereon with a releasing agent having an ability to release, such as silicone; high-quality paper anchor-coated with a resin or laminated with polyethylene, further coated with a releasing agent having an ability to release, such as silicone; and so forth.

The pressure-sensitive adhesive component for an ankle of the present invention preferably has suitable kickback property, good handling property (workability), and fixability. Therefore, it is preferable that the pressure-sensitive adhesive component for an ankle of the present invention (for adhesive the pressure-sensitive adhesive component without the release liner, that is, pressure-sensitive adhesive component consisting of a support and a pressure-sensitive adhesive layer) has an elongation (degree of elongation) in a longitudinal direction (in the direction of larger length of a rectangle) of about 30% to about 110%, more preferably 30% to 70%. Such a pressure-sensitive adhesive component has a tensile strength of preferably 10 N/19 mm width or more and 200 N/19 mm width or less and a 20% modulus (tensile stress at 20% elongation) of preferably 0.5 N/19 mm width or more and 8 N/19 mm width or less. If the elongation is greater than 110%, there is the fear that the pressure-sensitive adhesive component in the region where it contacts the ankle portion is elongated to the limit by repeated expansion and contraction caused in response to the expansion and contraction motions of the ankle portion.

It is preferable that the substrate 14 that constitutes the pressure-sensitive adhesive component for an ankle of the present invention has a tensile stress at 20% elongation is 10 N/19 mm width or less and more preferably, from the viewpoint of fixability of ankle joint and the like, 9 N/19 mm width or less. Further, it is preferable that the substrate has a hysteresis at 80% elongation of 85% or more and a tensile stress at 80% elongation of 15 N/19 mm width or more. To further alleviate the load on the ankle joint and the like, it is more preferable that the substrate has a hysteresis at 80% elongation of 88% or more and a tensile stress at 80% elongation of 16 N/19 mm width or more. The pressure-sensitive adhesive component for an ankle that contains the substrate having, such characteristics can realize followability and fixability to the ankle joint and the like.

Here, the term "hysteresis at 80% elongation" refers to an index that indicates restoration when the pressure-sensitive adhesive component for an ankle is expanded to 80% of the maximum elongation. On the other hand, the term "tensile stress at 20% elongation (20% modulus)" refers to a tensile strength when a sample having a predetermined form in elongated to 20% elongation at a predetermined speed, and the term "tensile stress at 80% elongation (80% modulus)" refers to a tensile strength when a sample having a predetermined form is elongated to 80% elongation at a predetermined speed.

It is preferable that the substrate 14 has a degree of elongation suitable for fixing the ankle joint and the like and examples of the material of such a substrate include non-woven fabrics, woven fabrics, high twist fabrics containing high twist yarn in the longitudinal direction, longitudinally expanding fabric containing elastic yarn as warp (for example, spandex fabric using an elastic yarn having urethane as a core of the yarn), elastic fabric using elastic yarn as warp and weft, made of nylon, polyester, polyurethane, rayon, polypropylene, polyethylene, cotton and so forth. In the present invention, in consideration of the above-mentioned characteristics, it is preferable that a knitted fabric having elasticity (hereinafter, referred to as "elastic knitted fabric") is used. For example, knitted fabric knitted from a single material selected from stretch yarn made of nylon, polyester and the like fibers subjected to special processing to impart elasticity therewith, or synthetic fiber yarn having high elasticity such as polyurethane elastic fiber or knitted fabric knitted from a mixture of such a synthetic fiber and a fiber having low elasticity such as polyester fiber or cotton, knitted fabric made of spun bond nonwoven fabric in which an elastic fiber such as polyurethane elastic yarn is knitted and so forth may be used. Knitting methods that can be used include (warp) knitting including tricot knitting, Rachel knitting, and Milanese knitting, and (weft) knitting including plain knitting and circular knitting. Among them, warp knit goods are more preferable since they do not fray when they are out. The thickness of the synthetic yarn is preferably about 40 to about 160 deniers.

The substrate 14 that constitutes the pressure-sensitive adhesive component for an ankle of the present invention may be made of natural rubber sheet and synthetic rubber sheet having elasticity, natural and synthetic rubber sheets provided with perforations to have moisture permeability, sheet made of the above-mentioned woven fabric or knitted fabric laminated with a polyurethane film and no forth. In the present invention, it is preferable to use a high twist fabric having a longitudinal elongation of about 30% to about 110%, a tensile strength of 10 N/19 mm width to 200 N/19 mm width, and a 20% modulus of 0.5 N/19 mm width to 10 N/19 width. Use of such a high twist fabric enables the pressure-sensitive adhesive component for an ankle to exhibit handling property (workability), followability, fixability, compressibility (kickback property) and so forth that are important when taping is performed.

It is preferable that the thickness of the substrate 14 is appropriately determined depending on the material characteristics and so forth of the substrate. In consideration of the followability to the skin, fixability of tape, workability of taping and so forth, the thickness of the substrate 14 is preferably 200 μm to 1,000 μm, more preferably, 300 μm to 1,000 μm, particularly preferably 300 μm to 800 μm, and most preferably 500 μm to 800 μm. The substrate 14 may be either of a single layer structure or of a double layer structure. In the came of multi-layer structures, it is preferable that the total thickness of all the layers is within the above-mentioned range.

Further, it is preferable that the pressure-sensitive adhesive component for an ankle of the present invention has a thickness of the pressure-sensitive adhesive component without the release liner is 300 µm to 1,100 µm.

The substrate 14 is provided with a polyurethane layer on its outer surface (in FIG. 1B, on a lower surface of the substrate 14). That is, in FIG. 2, the other layer 18 may be a polyurethane layer. Covering the outer surface of the substrate 14 with a polyurethane layer can impart the substrate 14 with moisture permeability and waterproof property.

The polyurethane layer may be ford from known urethanes such an ether-based urethanes and ester-based urethanes. In the present invention, polyurethane films may be used as the polyurethane layer. The thickness of the polyurethane layer is preferably 5 µm or more and less than 30 µm. When the thickness of the polyurethane layer is 5 µm or more, the unevenness of the surface of the substrate made of, for example, elastic knitted fabric and the like is sufficiently coated so that no pinholes are formed. On the other hand, when the thickness of the polyurethane layer is less than 30 µm, sufficient moisture permeability can be maintained.

For example, when the substrate is applied so as to overlap on the back surface of the same substrate having unevenness thereon, sometimes an end of the overlappingly applied pressure-sensitive adhesive component is turned. However, the adhesive power onto the own back surface of the substrate can be improved. Further, when the substrate having poor waterproof property is used in rain and is wetted, the applied portion tends to be peeled off. However, provision of the polyurethane layer can impart the substrate with waterproof property. Furthermore, adjustment of the thickness of the polyurethane layer can control the degree of the kickback property.

It is preferable that the pressure-sensitive adhesive layer 15 has flexibility and viscoelasticity such that it can follow up the skin onto which it is applied and is formed by using a pressure-sensitive adhesive having less stimulation to the skin. For this purpose, various pressure-sensitive adhesives well-known or practically used in the field of common pressure-sensitive adhesive tape for taping may be used. Specific examples of the pressure-sensitive adhesive that can be used include acrylic-based pressure-sensitive adhesives, rubber-based pressure-sensitive adhesives, synthetic rubber-based pressure-sensitive adhesives, vinyl ether-based pressure-sensitive adhesives, silicone-based pressure-sensitive adhesives, and gel-based pressure-sensitive adhesives. In consideration of stimulation to the skin and so forth, it is preferable that the acrylic-based pressure-sensitive adhesives and gel-based pressure-sensitive adhesives are used. For example, oily gel pressure-sensitive adhesives have relatively low adhesive power whereas they have excellent adherence to the skin and are satisfactory for use in taping and so forth. They can be used advantageously since they do not harm the horny layer of the skin upon peeling off. Reference is made to Published Translation of PCT Application No. 2000-513287.

The pressure-sensitive adhesive layer 15 may be provided on the entire surface or a part of the surface one side of the substrate 14 (support 19). When it is provided on the surface of the support 19 partly, the pressure-sensitive adhesive layer may be formed as dots or stripes. The region where no pressure-sensitive adhesive layer is formed serves as an air passage as well. Therefore, the air permeability and moisture permeability of the pressure-sensitive adhesive component can be improved, so that steaming, skin irritation and so forth due to sweating can be prevented. The stripes may be of linear, undulated or the like forms. Generally, it is preferable that an undulated form that undergoes less variation with time in sectional area of inter-stripe interstices is adopted. However, it is preferable that the form of the stripes may be determined appropriately depending on the characteristics and so forth of the pressure-sensitive adhesive to be used. On the other hand, when the pressure-sensitive adhesive layer is provided on the surface of the substrate partly, it is preferable that the size and arrangement of dots, the size of the inter-stripe interstices and so forth are appropriately designed such that a space that serves as an air passage can be assured between the adjacent stripes.

When the pressure-sensitive adhesive is coated on a desired region, for example, a pressure-sensitive adhesive layer having a desired streak-like or wave-like form may be formed on a release liner by using a mold having, for example, comb-like form with fixing or moving in amplitude the comb during coating and then the streak-like or wave-like form may be transferred on the surface of the substrate 14.

It is preferable that the thickness of the pressure-sensitive adhesive layer 15 is determined appropriately depending on the type, characteristics and so forth of the pressure-sensitive adhesive to be used; for example, the thickness of the pressure-sensitive adhesive layer 15 is preferably 20 µm to 120 µm and more preferably 40 µm to 100 µm.

The pressure-sensitive adhesive component for an ankle may be provided with perforations as necessary so far as they do not deteriorate the effects of the present invention.

Figure 3A:
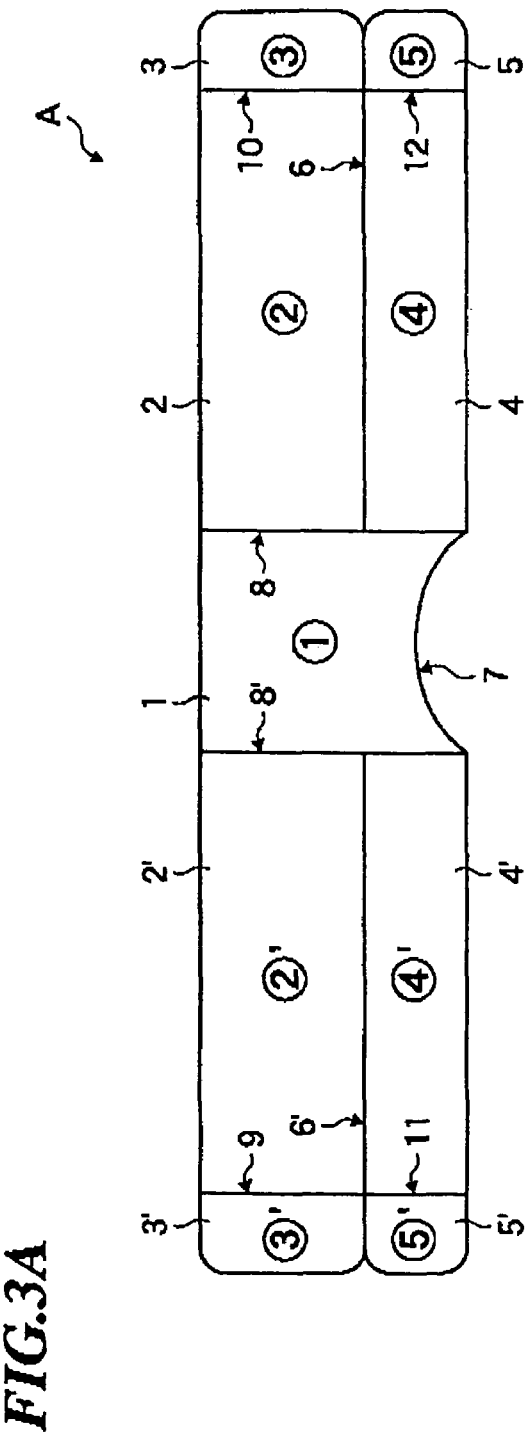
FIG. 3A is a plan view showing an H-shaped pressure-sensitive adhesive component A for an ankle according to a second embodiment of the present invention.
Figure 3B:
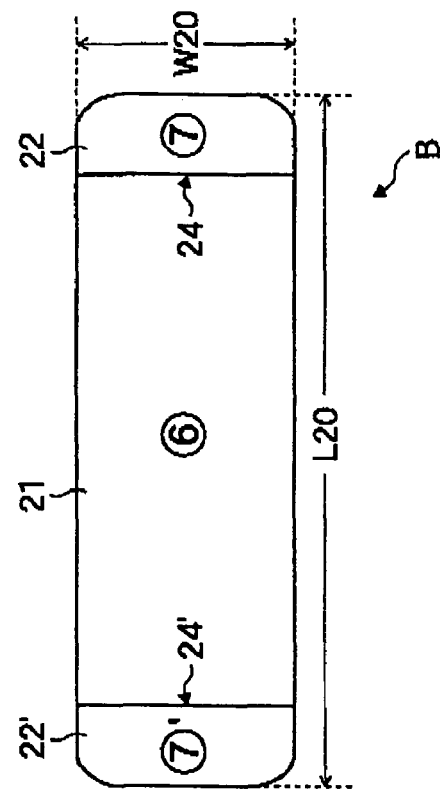
FIG. 3B is a plan view showing an auxiliary pressure-sensitive adhesive a component B.

Then, a pressure-sensitive adhesive component including, besides the H-shaped pressure-sensitive adhesive component, an auxiliary pressure-sensitive adhesive component as an independent member will be described. FIG. 3 shows a pressure-sensitive adhesive component for an ankle according to a second embodiment of the present invention, Here, the H-shaped pressure-sensitive adhesive component shown in FIG. 3A is the same as the H-shaped pressure-sensitive adhesive component A shown in FIG. 1A. The auxiliary pressure-sensitive adhesive component B shown in FIG. 3B has a structure that includes a tape portion 21 and a right-hand side edge 22 and a left-hand side edge 22' on both ends thereof. The right-hand edge 22 and left-hand edge 22' are tongue-shaped, with the corner portions thereof being cut off. Forming edge portions into a tongue shape makes them difficult to be peeled off when applied in an overlapping manner one on another. Thus, the auxiliary pressure-sensitive adhesive component B has a substantially rectangular contour with the corners being constituted by R-shaped curves.

The pressure-sensitive adhesive component has a shorter rectangular edge length (W20) of preferably 50 mm to 100 mm and a longer rectangular edge length (L20) of preferably 100 mm to 350 mm. It is preferable that the pressure-sensitive adhesive component is designed appropriately within the above-mentioned range in consideration of the body type, foot type and so forth.

The layer structure of the auxiliary pressure-sensitive adhesive component shown in FIG. 3B is the same as that of the pressure-sensitive adhesive component shown in FIG. 3A, that is, the same as that of the pressure-sensitive adhesive component shown in FIG. 1B; that is, the auxiliary pressure-sensitive adhesive component includes a substrate having thereon a pressure-sensitive adhesive layer and a release liner on the pressure-sensitive adhesive layer. The release liner that covers the pressure-sensitive adhesive layer is provided with back slits at a boundary 24 between the tape portion 21 and the right-hand side edge portion 22 and at a boundary 24' between the tape portion 21 and the left-hand aid edge portion 22'. Further, similar to FIG. 1A, numerical symbols (⑥, ⑦, etc.) are printed on each part of the release liner provided with back slits. The numerical symbols to be printed on the release liner of the auxiliary pressure-sensitive adhesive component may be continuous to those shown in FIG. 3A.

As one example of the method of performing taping by using the pressure-sensitive adhesive component for an ankle of the present invention, an example in which a pressure-sensitive adhesive component for an ankle having the H-shaped pressure-sensitive adhesive component A and the auxiliary pressure-sensitive adhesive component B as shown in FIGS. 3A and 3B is applied to the ankle will be described hereinbelow. In the present invention, the term "taping" refers to fixing a treatment site such as a joint, muscle or tendon by using a pressure-sensitive adhesive tape and the like and supporting, correcting, reinforcing and so forth the treatment site exhibit the effects of alleviating the pain and promoting the therapy.

FIGS. 4A to 7B are diagrams that illustrate the method of fixing an ankle joint and the like by using the pressure-sensitive adhesive component for an ankle according to the second embodiment of the present invention. FIGS. 4A to 7B illustrate the method of applying the H-shaped pressure-sensitive adhesive component A (hereinafter, sometimes referred to as "method A") and FIGS. 7A and 7B further illustrate the method of further applying the auxiliary pressure-sensitive adhesive component B (hereinafter, sometimes referred to as "method B"). Therefore, when the taping is performed by using the pressure-sensitive adhesive component for an ankle including only the H-shaped pressure-sensitive adhesive component shown in FIGS. 1A and 1B, the anterior half of the use method just before the application of the auxiliary pressure-sensitive adhesive component B (method A) may be applied as it in to the use method shown below.

Figure 4A:
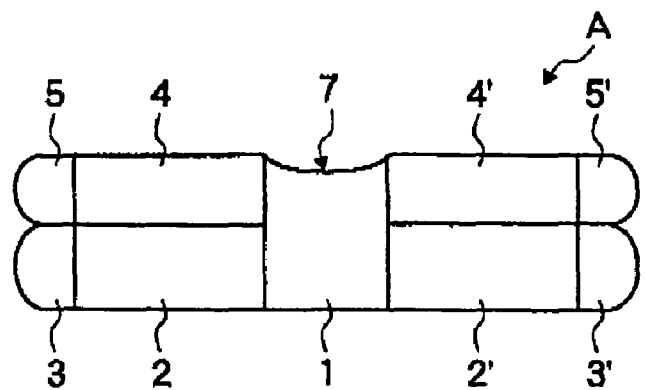
FIG. 4A is a plan view showing an H-shaped pressure-sensitive adhesive component A for illustrating a method of performing taping according to the present invention.
Figure 4B:
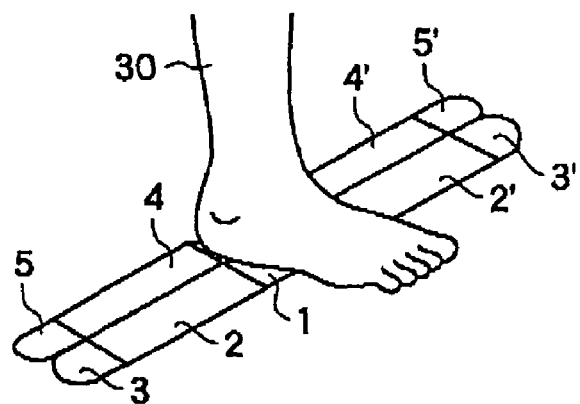
FIGS. 4B and 4C are each a schematic perspective view illustrating the method of performing taping using the H-shaped pressure-sensitive adhesive component A according to the present invention.
Figure 4C:
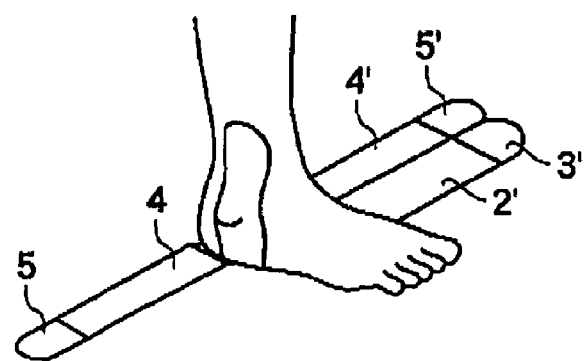
Figure 5A:
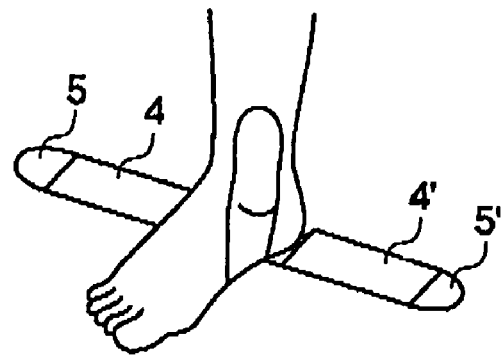
FIGS. 5A, 5B and 5C are each a schematic perspective view illustrating the method of performing taping using the H-shaped pressure-sensitive adhesive component A according to the present invention subsequent to the steps shown in FIGS. 4A to 4C.
Figure 5B:
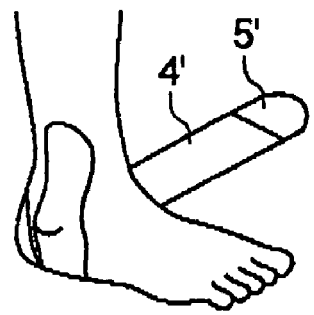
Figure 5C:
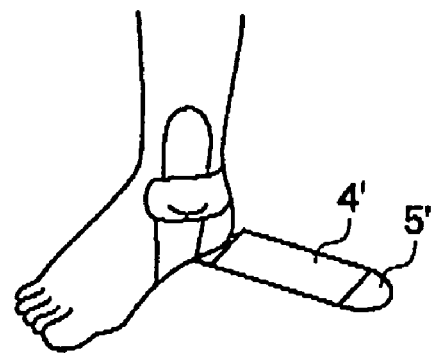

In FIG. 4A, an H-shaped pressure-sensitive adhesive component A is placed on a stage that facilitates the operation of application, such as a footrest, with the release liner being placed upside. After the release liner (marking ①) on the bottom portion 1 is removed, the heel sole is mounted on the pressure-sensitive adhesive layer of the bottom portion and applied thereto such that the rear part of the heel is protruded from the concave edge 7 of the bottom portion 1 (see FIG. 4B). The release liner (marking ②) on the first front tape portion 2 to be applied to the outside of the ankle portion is removed, and the first front tape head portion 3 is hold by the hand and in applied from the heal toward the knee joint so as to cover the lateral malleolus of the ankle joint while expanding the first front tape portion, followed by removal of the release liner (marking ③) on the first front head portion 3 and application of the pressure-sensitive adhesive component (see FIG. 4C). Subsequently, as shown in FIG. 5A, the release liner (marking ②') on the second front tape portion 2' to be applied to the inside of the ankle portion, and the second front tape portion 2' is applied while drawing it just above so as to cover the medial malleolus, followed by removal of the release liner (marking ③') on the second front tape head portion 3' and application of the head portion. This operation corresponds to so-called "stirrup", which can suppress and limit varus of ankle bone and caloaneal bone. Then, as shown in FIGS. 5B and 5C, the release liner (marking ④) on the first rear tape portion 4 positioned on an outer side of the ankle portion is removed, and the first rear tape head portion 5 is hold by the hand while expanding the first rear tape portion and is applied by passing along the back of the ankle joint so as to cover over the medial malleolus, followed by removal of the release liner (marking ⑤) on the first rear tape head portion 5 and application of the head portion. Then, as whom in FIGS. 6A and 6B, the release liner (marking ④') on the second rear tape portion 4' positioned on an inner side of the ankle joint is removed, and the second rear tape head portion 5' in hold by the hand while expanding the second rear tape portion and is applied by passing along the back of the ankle joint so as to cover over the lateral malleolus, followed by removal of the release liner (marking ⑤') on the second rear tape head portion 5' and application of the head portion. This operation corresponds to so-called "heel lock", which exhibits not only the taping function of stirrup but also suppresses and limits the varus of the foot joint so that movement of the ankle bone forward can be suppressed and limited. Thus, the method of applying the H-shaped pressure-sensitive adhesive component A to the ankle portion is referred to as "method A" for convenience's sake.

Subsequently, the release liner (marking ⑦) on one edge portion 22 of the auxiliary pressure-sensitive adhesive component B is removed, and the auxiliary pressure-sensitive adhesive component is applied onto the H-shaped pressure-sensitive adhesive component A in an overlapping manner so as to cover the foot from the dorsum of foot to the lateral malleolus. Thereafter, the release liner (marking ⑥) on the tape portion 6 is roved and the tape portion 6 is applied while expanding the tape portion 6 by drawing it so as to cover an Achilles' tendon of a back of the ankle. Finally, after the release liner (marking ⑦') on the remaining edge portion 22' is removed, the edge portion 22' is applied so as to cover the medial malleolus and further cover the dorsum of foot (see FIGS. 7A and 7B). This operation corresponds to so-called "half eight". Thus, the method in which after the H-shaped pressure-sensitive adhesive component A is applied, further the auxiliary pressure-sensitive adhesive component B is applied to the ankle portion is referred to as "method B" for convenience's sake.

Use of the pressure-sensitive adhesive component for an ankle shown in FIG. 3 according to the present invention enables appropriate fixing of ankle joints and the like by the taping according to the method A. Further, use of the auxiliary component and performing taping in an overlapping manner can protect the Achilles' tendon and strengthen the fixing power of the ankle portion. Furthermore, the present invention can play a role of fixing the first tape portion of the H-shaped pressure-sensitive adhesive component. In addition, the taping may be performed by moderately loading the body weight on the bottom portion as necessary. This allows taping to be performed in a state close to the state of the ankle joint upon which a load is imposed when exercising.

FIG. 8A is a plan view showing a pressure-sensitive adhesive component for an ankle C according to a third embodiment of the present invention and FIG. 8B is a front view of the pressure-sensitive adhesive component for an ankle C shown in FIG. 8A. Here, a pressure-sensitive adhesive component for an ankle consisting of a modified H-shaped pressure-sensitive adhesive component having a substantially trapezoidal contour will be described.

In FIG. 8A, the pressure-sensitive adhesive component for an ankle has a substantially trapezoidal contour and a bottom portion 41 to be applied to the heel sole of the foot substantially in the center of the trapezoid. On both sides of the bottom portion 41, the pressure-sensitive adhesive component has a first tape-shaped body consisting of a first rear tape body 42 and a first front tape body 43, and a second tape-shaped body 47' consisting of a second rear tape body 42' and a second front tape 43', respectively. The axes of the first rear tape body 42 and the first front tape body 43' are parallel to each other. Similarly, the axes of the second rear tape body 42' and the second front tape body 43' are parallel to each other. The first rear tape body 42 and the second rear tape body 42' are tapes to be applied to aides of the ankle; they must have a length sufficient to cover the malleolus. However, it is preferable that they do not have too large a length but a suitable length, for example, a length on the order such that they can reach slightly above the malleolus. When the tapes are set to such a length, the pressure-sensitive adhesive component taped will not protrude from the upper end of the socks, thus giving an acceptable appearance. Note that users may cut the tapes so as to have such a length appropriately prior to use. The first front tape body 43 and the second front tape body 43' are tapes to be applied around the ankle so as to cover the Achilles' tendon and longer than the first and second rear tape bodies 42 and 42'.

Each of the head edges of the first rear tape body, first front tape body, second rear tape body, and second front tape body are tongue-shaped.

The bottom portion 41 are rectangular and the first rear tape body 42 and the first front tape body 43 are arranged on one aide of the rectangle and the second rear tape body 42' and the second front tape body 43' are arranged on the opposite aide of the rectangle. Note that the edge on the side of the rear tape body of the bottom portion 41 may be formed into a concave form.

The layer structure of the modified H-shaped pressure-sensitive adhesive component C shown in FIG. 8A, which will be exemplified in FIG. 8B, may assume the ale structure as that of the layer construction shown in FIG. 2. Here, the release liner 16 may be omitted. However, it is preferable that the release liner 16 is laminated on the pressure-sensitive adhesive layer 15 in order to prevent the pressure-sensitive adhesive layer 15 from being contaminated with dust and dirt and protect adhesive power until use. The release liner 16 is provided with a back slit at several positions. For example, in FIG. 8A the back slits are provided at a boundary portion 44 between the bottom portion 41 and the first rear tape body 42 and the first front tape body 43 arranged on the left side of the bottom portion and similarly at a boundary portion 44' between the bottom portion 41 and the second tape body arranged on the right side of the bottom portion. In the case of this pressure-sensitive adhesive component for an ankle, numeric symbols (such as ① and ②) are printed and a printed portion 45 formed on the release liner of each part provided with back splits. Although this printed portions 45 are not limited to numerical symbols, it is preferable that images such as characters (including numerical symbols) showing the order of taping and illustrations are indicated by any appropriate method.

Further, in the present embodiment, similarly to the H-shaped pressure-sensitive adhesive component shown in FIG. 1, the first front tape body has a front tape portion and a front tape head portion and the first rear tape body has a rear tape portion and a rear tape head portion and boundary portions thereof may be provided with back slits, and in addition the release liner of each back alit part maybe formed with a printed part.

The substantially trapezoidal pressure-sensitive adhesive component for an ankle (modified H-shaped pressure-sensitive adhesive component C) shown in FIGS. 8 and 8B has a lower bottom side length, i.e., a length from the head edge of the first front tape body 43 to the head edge of the second front tape body 43' (L10) of 400 mm to 650 mm, and a trapezoidal height, i.e., the total (W10) of the width (W12) of the front tape bodies (43, 43') and the width W11 of the rear tape bodies (42, 42') is preferably 50 mm and 150 mm and it is preferable that the pressure-sensitive adhesive component for an ankle is appropriately designed within the above mentioned range taking into consideration the body type, foot type and so forth. The length (L11) of the rear tape body 42 (or 42') is preferably 80 mm to 150 mm and the length (L13) of the front tape body 43 (or 43') is preferably 200 mm to 270 mm. Further, the length (L12) of the bottom portion 41 may be greater than the width of the heal and is, for example, 50 mm to 90 mm. It is preferable that the lengths and size of the bottom portion and the like are appropriately designed in consideration of the body type, foot type and the like.

Figure 6A:
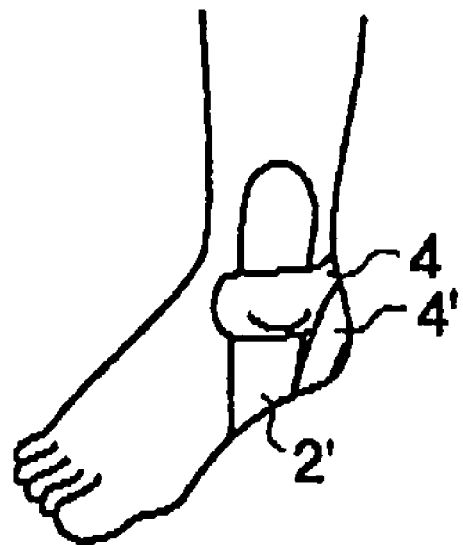
FIGS. 6A and 6B are each a schematic perspective view illustrating the method of performing taping using the H-shad pressure-sensitive adhesive component A according to the present invention subsequent to the steps shown in FIGS. 5A to 5C.
Figure 6B:
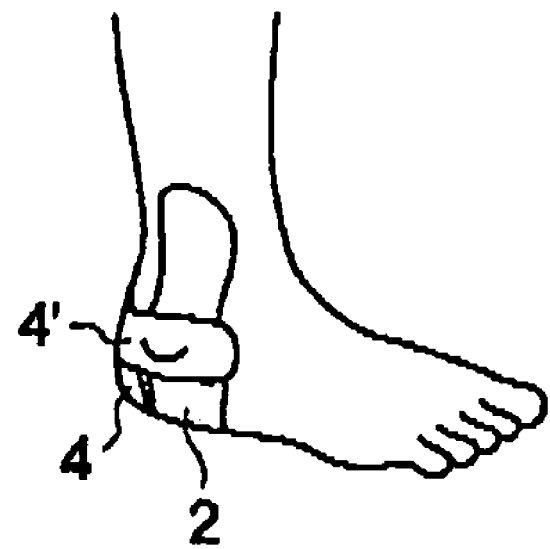
Figure 7A:
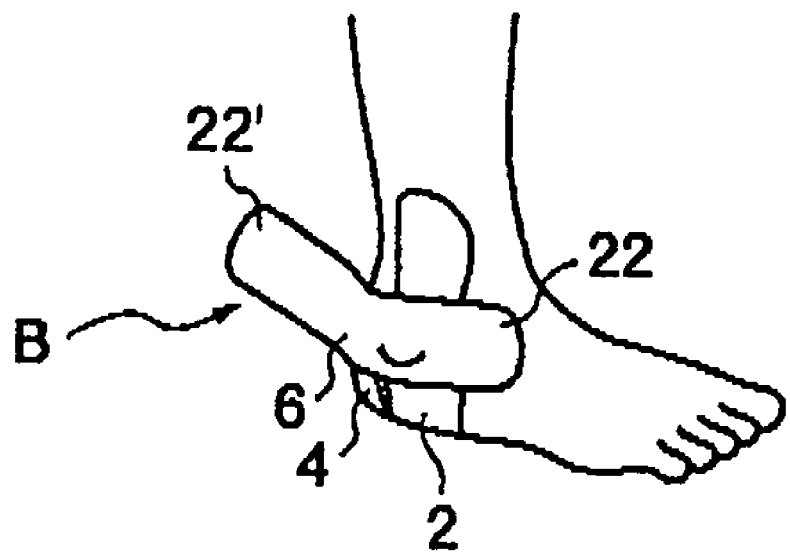
FIGS. 7A and 7B are each a schematic perspective view illustrating a method of performing taping using an auxiliary pressure-sensitive adhesive component B according to the present invention.
Figure 7B:
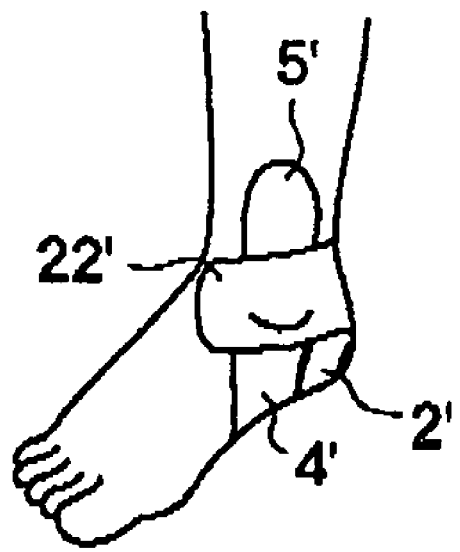

As one example of the method of performing taping by using the pressure-sensitive adhesive component for an ankle of the present invention, an example in which a modified H-shaped pressure-sensitive adhesive component for an ankle having a substantially trapezoidal shape as shown in FIGS. 6A and 6B in applied to the ankle portion will be described hereinbelow.

FIGS. 9A to 11C are diagrams that illustrate the method of fixing an ankle joint and the like by using the pressure-sensitive adhesive component for an ankle according to the third embodiment of the present invention (modified H-shaped pressure-sensitive adhesive component C) (hereinafter, sometimes referred to as "method C").

Figure 9A:
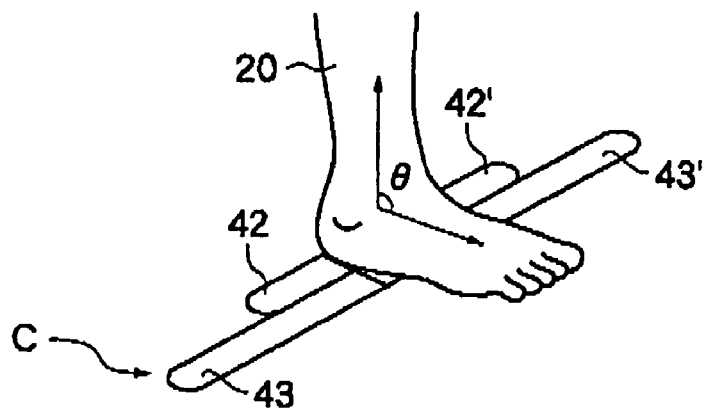
FIG. 9A, 9B and 9C are each a schematic perspective view illustrating a method of performing taping using a modified H-shaped pressure-sensitive adhesive component C according to the present invention.
Figure 9B:
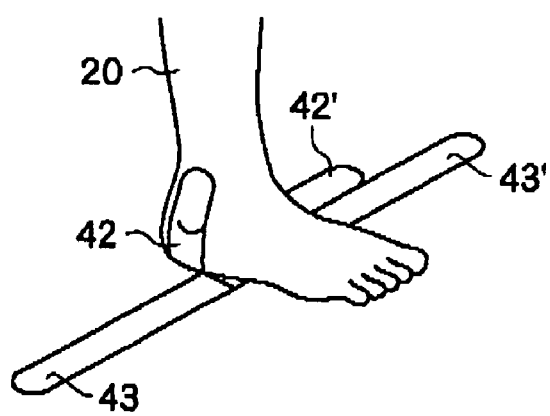

In FIG. 9A, a pressure-sensitive adhesive component is placed on a place that facilitates the operation of application, such as floor or ground, with the release liner being placed upside. After the release liner (marking ①) on the bottom portion 41 is removed, the heel sole in mounted on the pressure-sensitive adhesive layer of the bottom portion 41 and applied thereto such that the rear tapes 42 and 42' pass just above the malleolus when they are lifted up, that is, the heel is slightly protruded from the rear side of the bottom portion. 41 (the upper side of the trapezoid). In FIG. 9B, the release liner (marking ②) on the first rear tape body 42 to be applied to the outside of the ankle portion is removed while maintaining the angle (θ) of the ankle portion at 90°, the head portion of the first rear tape body 42 is held by the hand and pulled immediately above, and the first rear tape body 42 is applied halfway so as to cover the lateral malleolus of the ankle joint while expanding the first rear tape body 42, and then the head portion of the first rear tape body 42 is applied in a less elongated state than ever. The reason why the tape body is applied halfway in an elongated state is to impart a moderate fixing power to the treatment site and application after the elongation of the head portion is lessened is to decrease physical stress due to the contact area between the akin and the pressure-sensitive adhesive component to thereby alleviating the skin irritation and reducing peeling off of the edge of the tape body due to strain-stress.

Figure 9C:
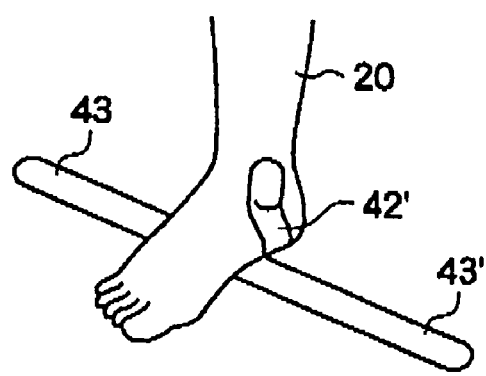

Subsequently, as shown in FIG. 9C, after the release liner (marking ②') on the second rear tape body 42' to be applied to the inner side of the ankle portion is removed, the head portion of the tape is held by the hand and the second rear tape body 42' is applied halfway while drawing it just above so as to cover the actual malleolus, and then the elongation of the head portion of the second rear tape body 42' is lessened, followed by applying the head portion of the tape body 42'. This operation corresponds to so-called "stirrup", which can suppress and limit varus of the calcaneal bone and ankle bone.

Figure 10A:
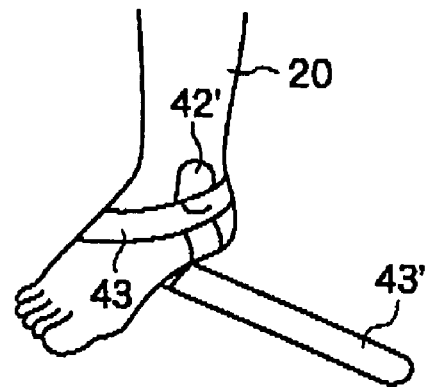
FIGS. 10A, 10B and 10C are each a schematic perspective view illustrating the method of performing taping using the modified H-shaped pressure-sensitive adhesive component C according to the present invention subsequent to the steps shown in FIGS. 9A to 9C.
Figure 10B:
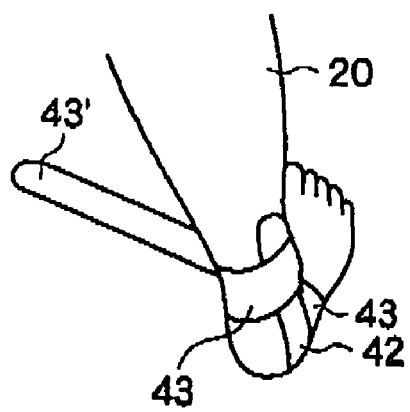
Figure 10C:
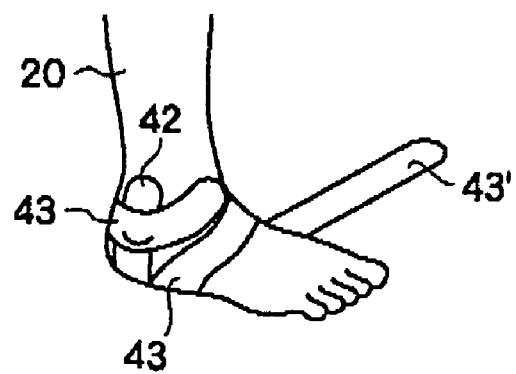

Then, as shown in FIG. 10A, the release liner (marking ③) on the first front tape body 43 to be applied to the outside of the ankle portion is removed, and the head portion of the first front tape body 43 in held by the hand while expanding the first front tape body and is applied by passing along the dorsum of the ankle an back of the ankle joint so as to cover the Achilles' tendon, to the front of the ankle, that is by making the first front tape body 43 to wind substantially around the ankle, followed by applying the first front tape body 43 except for the head portion thereof, and subsequently loosening the elongation of the head portion and then applying the head portion (see FIG. 10C).

Figure 11A:
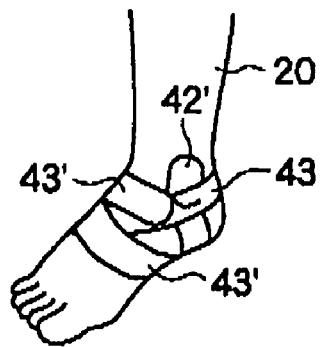
FIGS. 11A, 11B and 11C are each a schematic perspective view illustrating the method of performing taping using the modified H-shaped pressure-sensitive adhesive component C according to the present invention subsequent to the steps shown in FIGS. 10A to 10C.
Figure 11B:
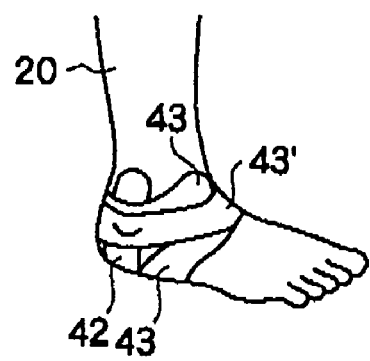
Figure 11C:
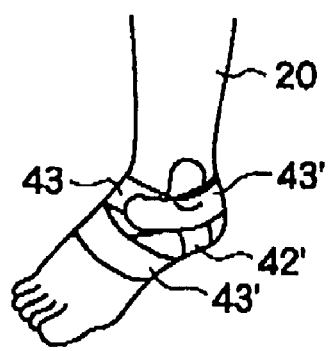

Similarly, as shown in FIG. 11A, after the release liner (marking ③') on the second front tape body 43' to be applied to the inner side of the ankle joint in removed, the head portion of the second front tape body 43' is hold by the hand and the second front tape body 43' except for the head portion is applied while drawing it to pass the dorsum of foot and back of the ankle joint 80 as to cover the Achilles' tendon (see FIG. 11B) to thereby making the head portion of the second front tape body to wind substantially around the ankle, and then the elongation of the head portion of the second front tape body 43' in lessened and the head portion thereof is applied to the substrate of the already applied first tape body 43 in an overlapping manner (see FIG. 11C). This operation corresponds to so-called "figure eight",which can exhibit the stirrup taping function and also suppressing and limiting the varus of the ankle joint of suppress and limit varus of the caloaneal bone and ankle bone, thee preventing the forward movement of the ankle bone. Further, it has the function of protecting the Achilles' tendon, strengthening the fixing power of the ankle portion to fix the stirrup taping.

In addition, the taping may be performed by moderately loading the body weight on the bottom portion as necessary. This allows taping to be performed in a state close to the state of the ankle joint upon which a load is imposed when exercising.

According to the present invention, taping by using the modified H-shaped pressure-sensitive adhesive component having a substantially trapezoidal contour can fix the ankle joint and the like appropriately as described above.

Figure 12A:
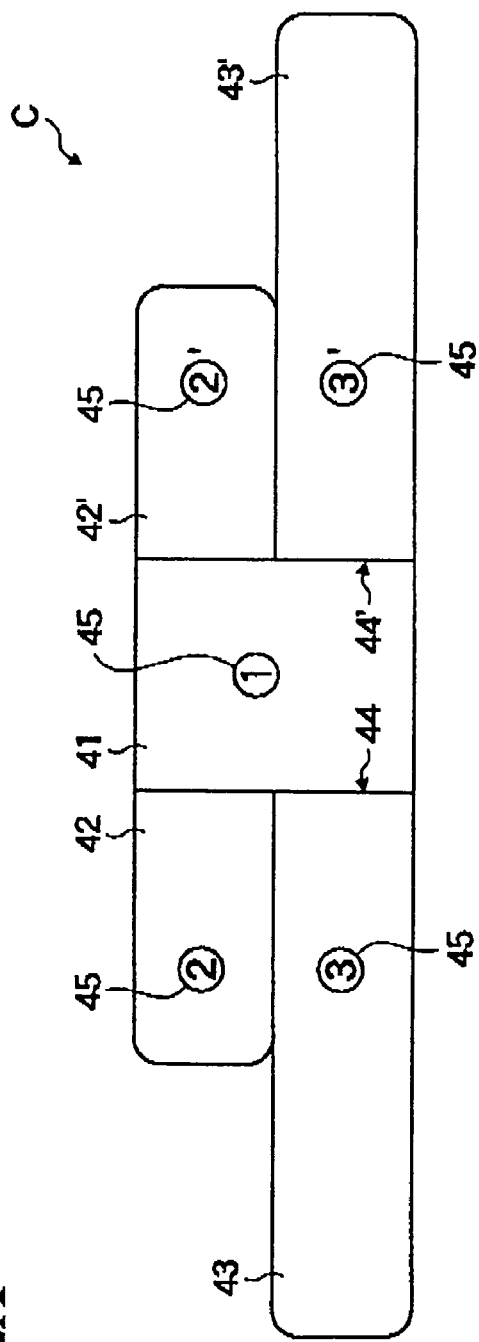
FIG. 12A is a plan view showing a pressure-sensitive adhesive component for an ankle according to a fourth embodiment of the present invention.
Figure 12B:
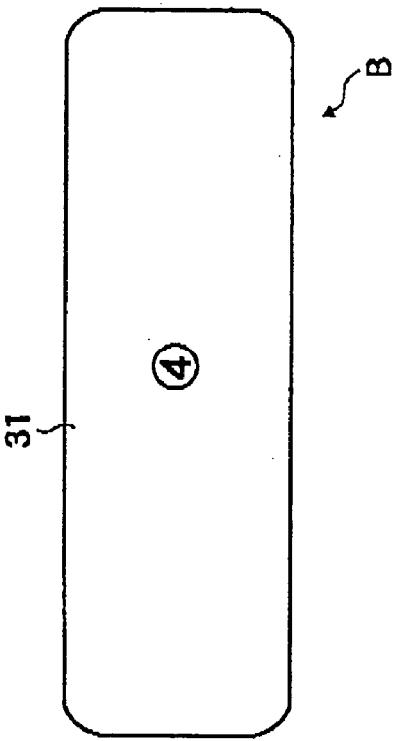
FIG. 12B is a plan view showing an auxiliary pressure-sensitive adhesive component B.

In the present invention, after performing taping by using a modified H-shaped pressure-sensitive adhesive component, a rectangular auxiliary component formed of nonelastic cotton tape or elastic tape as shown in FIG. 3B may be appropriately used and taped on the modified H-shaped pressure-sensitive adhesive component in an overlapping manner to reinforce the taping by the modified H-shaped pressure-sensitive adhesive component. The embodiment in which the auxiliary pressure-sensitive adhesive component B is used in combination with the modified H-shaped pressure-sensitive adhesive component is shown in FIGS. 12A and 12B. In FIGS. 12A and 12B, an auxiliary pressure-sensitive adhesive component 31 is of a substantially rectangular shape and preferably has a size such that the dorsum of the foot and the Achilles' tendon can be covered. For example, it is preferable that the rectangular shorter side is 3.8 cm to 7.5 cm long and a longer side is 7.5 cm to 20 cm long. Further, it is preferable that the edges of the rectangle are tongue-shaped. When the auxiliary pressure-sensitive adhesive component is constituted by an elastic tape, it may be made of a material similar to the modified H-shaped pressure-sensitive adhesive component C of the present invention and may have a similar layer structure. Further, when the auxiliary pressure-sensitive adhesive component is constituted by a nonelastic tape, it may be made of a material similar to that of a nonelastic cotton tape for general taping. Alternatively, the auxiliary pressure-sensitive adhesive component may be substituted by a commercially available tape for taping.

Hereinafter, the reinforcing method of performing taping by using the auxiliary pressure-sensitive adhesive component B (hereinafter, sometimes referred to as "method D") will be described. Note that although the auxiliary pressure-sensitive adhesive component is applied to the previously applied modified H-shaped pressure-sensitive adhesive component in an overlapping manner, the figure illustrating the auxiliary pressure-sensitive adhesive component and the modified H-shaped pressure-sensitive adhesive component in an overlapping state is complicated, so that hereinafter, explanation will be made with referring to diagrams in which the previously applied modified H-shaped pressure-sensitive adhesive component is omitted and only the auxiliary pressure-sensitive adhesive component is shown.

Figure 13A:
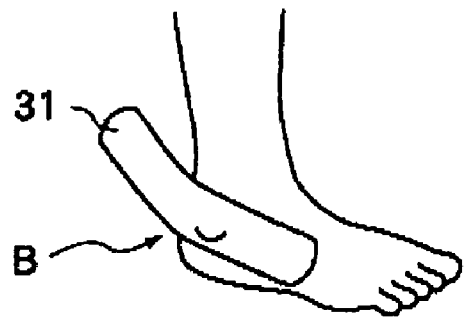
FIGS. 13A and 13B are each a schematic perspective view illustrating a method of performing taping further using an auxiliary pressure-sensitive adhesive tape B.
Figure 13B:
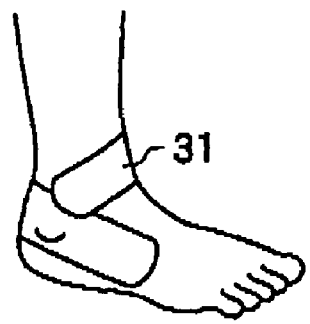

FIGS. 13A and 13B are diagrams that illustrate a first taping reinforcing method by using an auxiliary pressure-sensitive adhesive component. The method is an effective taping reinforcing method in preventing inward twist of the ankle i.e., varus of the ankle. In FIG. 13A, the auxiliary pressure-sensitive adhesive component 31 is passed starting from the base of the toes while expanding the auxiliary pressure-sensitive adhesive component 31 so as to cover the lateral malleolus and then passed along the back of the ankle to cover the Achilles' tendon, and along the inner side to the front side of the ankle as shown in FIG. 13B, followed by relaxation of elongation of the head portion and application.

Figure 14A:
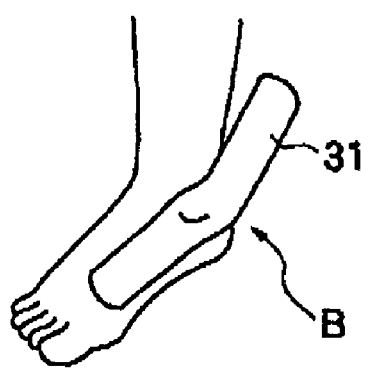
FIGS. 14A and 14B are each a schematic perspective view illustrating a method of performing taping further using an auxiliary pressure-sensitive adhesive tape B.
Figure 14B:
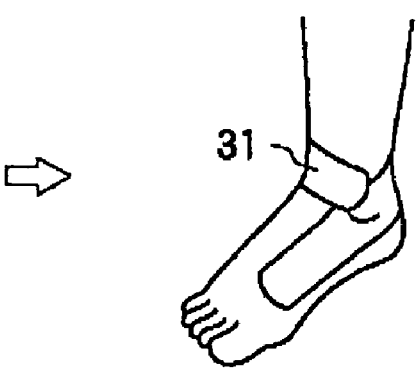

In FIGS. 14A and 14B, a second taping reinforcing method by using an auxiliary pressure-sensitive adhesive component is illustrated. The method is an effective taping reinforcing method in preventing outward twist of the ankle, i.e., valgus of the ankle. In FIG. 14A, the auxiliary pressure-sensitive adhesive component 31 is passed starting from the base of the toes while expanding the auxiliary pressure-sensitive adhesive component 31 so as to cover the medial malleolus and then passed along the back of the ankle to cover the Achilles' tendon, and along the outer side to the front side of the ankle as shown in FIG. 14B, followed by relaxation of elongation of the head portion and application.

Figure 15A:
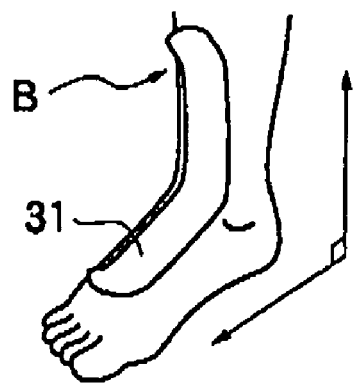
FIGS. 15A and 15B are each a schematic perspective view illustrating a method of performing taping further using an auxiliary pressure-sensitive adhesive tape B.
Figure 15B:

In FIGS. 15A and 15B, a third taping reinforcing method by using an auxiliary pressure-sensitive adhesive component is illustrated. The method is an effective taping reinforcing method in preventing twist of the ankle toward the floor, i.e., bending down of the toe of the ankle. In FIG. 15A, after the angle of the ankle is set to 90°, the auxiliary pressure-sensitive adhesive component 31 is applied to the base of the ankle and while holding this portion one free end of the pressure-sensitive adhesive component is pulled toward the tiptoe and applied halfway, followed by relaxation of elongation of the head portion and application to the base of the toes. Subsequently, an shown in FIG. 15B, while holding this portion another free end of the pressure-sensitive adhesive component is pulled toward the shin and applied halfway, followed by relaxation of elongation of the head portion and application to the shin.

Figure 16A:
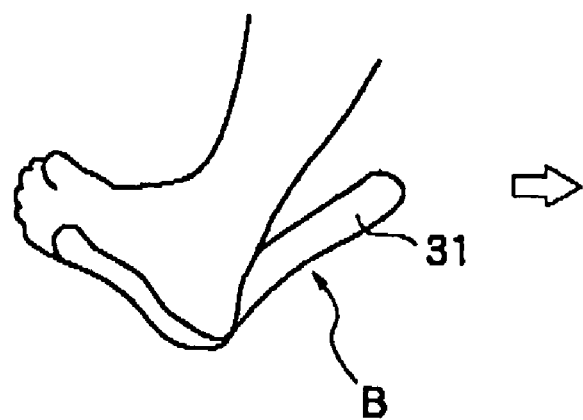
FIGS. 16A and 16B are each a schematic perspective view illustrating a method of performing taping further using an auxiliary pressure-sensitive adhesive tape B.
Figure 16B:

In FIGS. 16A and 16B, a fourth taping reinforcing method by using an auxiliary pressure-sensitive adhesive component is illustrated. The method is an effective taping reinforcing method in preventing twist of the ankle toward the shin, i.e., bending back of the toe of the ankle. In FIG. 16A, after the toe of the ankle is bent backward, that is, the angle of the ankle is set to an angle slightly smaller than 90°, the auxiliary pressure-sensitive adhesive component 31 is applied to the bas of the toes toward the bottom of the foot while expanding the auxiliary pressure-sensitive adhesive component 31. Then, as shown, in FIG. 16B, the auxiliary pressure-sensitive adhesive component 31 is applied from the backside of the ankle toward the shin while drawing it to expand with stretching the Achilles' tendon and applied halfway, followed by relaxation of elongation of the head portion and application of the pressure-sensitive adhesive component.

Use of the pressure-sensitive adhesive component for an ankle of the present invention shown in FIGS. 12A and 12B, enables fixing of the ankle joint and the like appropriately according to the taping method C. Further, overlapping taping by using the auxiliary pressure-sensitive adhesive component results in strengthening of the fixing power of the ankle portion.

Note that after taping the H-shaped pressure-sensitive adhesive component A according to the method A, reinforcing may be performed by using the auxiliary pressure-sensitive adhesive component according to one of the first to fourth reinforcing methods (method D) mentioned above instead of the method B. That is, in the present invention, the method D can be applied to the method A and the method B can be applied to the method C.

When markings indicating the order of application are shown on the release liners of the pressure-sensitive adhesive component for an ankle of the present invention and optional auxiliary pressure-sensitive adhesive component, application of the tapes in the order indicated enables users having no expert knowledge on taping to perform taping readily and at proper positions.

Further, in addition to the taping method of the present invention, a conventional taping method may also be used.

EXAMPLES

Hereinafter, the present invention will be described in more detail by examples. However, the present invention should not be considered as being limited to the samples and various applications are possible without departing from the spirit and scope of the present invention.

Example 1

A mixture of 90 parts by weight of 2-ethylhexyl acrylate and 9 parts by weight of acrylic acid was copolymerized with ethyl acetate under an inert gas atmosphere to obtain an acrylic-based pressure-sensitive adhesive. The acrylic-based pressure-sensitive adhesive was coated on a treated surface of a release liner having a high-quality paper laminated with a polyethylene, further subjected to treatment with silicone on the laminated surface to a thickness of 80 μm on dry basis and the resultant was dried at 120° C. for 3 minutes to form a pressure-sensitive adhesive layer. On this pressure-sensitive adhesive layer was superposed and applied an elastic knitted fabric having a thickness of 450 μm prepared by knitting 75-denier polyester yarn by interlock weaving so as to expand and contract to obtain a laminate having a layer structure of substrate/pressure-sensitive adhesive layer/release liner. The elastic knitted fabric had a tensile stress at 20% elongation of 2.5 N/19 mm width and a hysteresis at 80% elongation of 92%, and a tensile stress at 80% elongation of 19 N/19 mm width.

The obtained laminate was punched to obtain a pressure-sensitive adhesive component made of an H-shaped pressure-sensitive adhesive component and an auxiliary pressure-sensitive adhesive component having a shape as shown in FIGS. 3A and 3B. Note that the rectangular contour of the H-shaped pressure-sensitive adhesive component had the following sizes. The length of the shorter edge (W10) was 90 mm, and the length of the longer edge (L10) was 410 mm. The length of the bottom portion was 70 mm and the length of the tape portion was 140 mm. W11:W12=5:4. Further, the length (L20) of the auxiliary pressure-sensitive adhesive component was 250 mm and the width (W20) of the auxiliary pressure-sensitive adhesive component was 70 mm. The release liners were provided with back slits at each boundary of two adjacent parts of the release liner and was stamped continuous numbers indicating the order of application.

By using the obtained pressure-sensitive adhesive component for an ankle, taping on the ankle portion was performed according to the above-mentioned method A.

Example 2

An oily gal pressure-sensitive adhesive agent was coated on a treated surface of a release liner composed of polyethylene laminated high-quality paper, further treated with silicone, to a thickness of 70 μm on dry basis and was dried at 120° C. for 3 minutes to form a pressure-sensitive adhesive layer. An elastic knitted fabric having a thickness of 450 μm having the same material as the substrate in Example 1, knitted by interlock weaving 75 denier polyester yarn so that it could sand and contract was superposed and applied on the pressure-sensitive adhesive layer to obtain a laminate having a layer structure of substrate/pressure-sensitive adhesive layer/release liner.

The obtained laminate was punched to obtain a pressure-sensitive adhesive component mad of an H-shaped pressure-sensitive adhesive component and an auxiliary pressure-sensitive adhesive component having shape as shown in FIGS. 3A and 3B. Note that the rectangular contour of the H-shaped pressure-sensitive adhesive component had the following sizes. The length of the shorter edge (W10) was 90 mm, and the length of the longer edge (L10) was 450 mm. The length of the bottom portion was 70 mm and the length of the tape portion was 170 mm. W11 was 50 mm and W12 was 40 mm. Further, the length (L20) of the I-shaped auxiliary pressure-sensitive adhesive component was 200 mm and the width (W20) of the auxiliary pressure-sensitive adhesive component was 50 mm. In the same manner as in Example 1, the release liners were provided with back slits and stamped continuous numbers.

By using the obtained pressure-sensitive adhesive components (H-shaped pressure-sensitive adhesive component and auxiliary pressure-sensitive adhesive component), taping of an ankle portion was performed according to the above-mentioned method B.

Example 3

A pressure-sensitive adhesive layer was prepared in the same manner as in Example 1. A fabric (high twist fabric) obtained by twill weaving a mixed yarn composed of cotton and rayon prepared in advance as a substrate was superposed and laminated on the pressure-sensitive adhesive layer to obtain a laminate having a layer structure of substrate/pressure-sensitive adhesive layer/release liner. Note that the thickness of the substrate and the pressure-sensitive adhesive layer was 750 μm.

The obtained laminate was punched to obtain a pressure-sensitive adhesive component for an ankle having a shape as shown in FIGS. 8A and 8B. Note that the substantially trapezoidal contour of the modified H-shaped pressure-sensitive adhesive component had the following sizes. The height of the trapezoid in FIG. 8A (W10) was 100 mm, and the width of the rear tape body (W11) and the width of the front tape body (W12) were each 50 mm. The length of the lower edge of the trapezoid (L10) was 550 mm. Further, the length of the rear tape body (L11) was 115 mm. The length of the front tape body (L13) was 240 mm. In addition, the length of the bottom portion (L12) was 70 mm.

The release liners provided with back slits were stamped with continuous numbers indicating the order of application.

By using the obtained pressure-sensitive adhesive components, taping of an ankle portion was performed according to the above-mentioned taping method C for the modified H-shaped pressure-sensitive adhesive component.

Example 4

An oily gel pressure-sensitive adhesive agent was coated on a treated surface of a release liner composed of polyethylene laminated high-quality paper, further treated with silicone, to a thickness of 65 μm on dry basis and was dried at 120° C. for 3 minutes to form a pressure-sensitive adhesive layer. An about 13-μm polyurethane film was bonded and laminated on one surface of a substrate, i.e., an elastic knitted fabric having a thickness of about 252 μm prepared by nitting 75 denier polyeser yarn by interlock weaving so as to expand and contract to form a support. Superposing and applying the pressure-sensitive adhesive layer on the substrate side of the support formed a laminate having a layer structure of polyurethane film/substrate/pressure-sensitive adhesive layer/release liner. Note that the thickness of the laminate (excluding the release liner), specifically a total of the thicknesses of the support and the pressure-sensitive adhesive layer was about 320 μm.

The obtained laminate was punched to obtain a pressure-sensitive adhesive component for an ankle having a shape as shown in FIGS. 8A and 8B. Note that the substantially trapezoidal contour of the modified H-shaped pressure-sensitive adhesive component had the following sizes. The height of the trapezoid in FIG. 8A (W10) was 100 mm, and the width of the rear tape body (W11) and the width of the front tape body (W12) were each 50 mm. Tho length of the lower edge of the trapezoid (L10) was 560 mm. Further, the length of the rear tape body (L11) was 90 mm. The length of the front tape body (L13) was 255 mm. In addition, the length of the bottom portion (L12) was 50 mm.

The release liners provided with back slits were stamped with continuous numbers indicating the order of application.

By using the obtained pressure-sensitive adhesive components, taping of an ankle portion was performed according to the above-mentioned taping method C for modified H-shaped pressure-sensitive adhesive component.

Comparative Example 1

By using a conventional tape generally known as a taping tape for sports, taping was performed by a common method. That is , first an underlap tape was applied centered on the ankle Then two anchor tapes (38 mm in width), i.e., nonelastic cotton tapes, were applied on positions about 5 cm above the ankle. The two anchor tapes were applied off to the side by about ⅓ to about ½ or spirally wound around. Then, three stirrup tapes (38 mm in width) were applied by drawing up from the position of the inner anchor tape passing the medial malleolus to the position of the outer side anchor tape. Note that three stirrup tapes were applied off to the side by about ⅓ to about ½. Thereafter, to fasten the ends of the stirrup tapes with tho anchor tapes, the two anchor tapes were wound around at the position of about 5 cm above the ankle. Then, to prevent tottering of the ankle by pressing the periphery of the ankle, a figure eight tape was applied by winding it around the foot starting from the position of the Achilles' tendon passing the lateral malleolus and around the dorsum of foot, passing the plantar arch, crossing the dorsum of foot, passing above the medial malleolus, returning to the original point, and further running over the Achilles' tendon to the outer side to make a half round trip. Thereafter, heel lock taping was performed. That is, an elastic tape made of a high twist fabric was made to pass from the dorsum of foot as an original point, medial malleolus, back side of the heel, underneath the lateral malleolus, to the plantar arch, and crossing the dorsum of foot. Subsequently, the elastic tape was made to pass above the latenal malleolus, the Achilles' tendon to the heel, underneath the medial malleolus, obliquely passing the plantar arch, and then the dorsum of foot. This operation was performed repeatedly and the tape was continuously wound around the foot upward to the position where the anchor tape was applied above the ankle.

Twenty volunteers of thirties in age were asked to apply pressure-sensitive adhesive components around their ankles by the taping methods of Examples 1 to 4 and Comparative Example 1 and evaluate the operability of taping and the conditions immediately after the taping according to the standards described below. Further, after exercising jogging for 1 hour after applying the pressure-sensitive adhesive components, stability of adhesion and fixability after the exercise were evaluated according to the standards described below. The number of persons meeting each standard is shown in Table 1 and Table 2.

<Standards of Evaluation>

① Operability of Taping

[1]: Very easy to apply, cases in which taping could be performed within 3 minutes;

[2]: Difficult to apply, taping time being longer than 3 minutes and less than 10 minutes;

[3]: Very difficult to apply, cases in which taping took 10 minutes or longer.

② Conditions Immediately after Taping

[1]: No local thickening, very comfortable;

[2]: After the application, no discomfort but a slight feeling of strangeness being felt;

[3]: After the application, discomfort of being aware of taping, with some pain;

[4]: Very painful and discomfortable, unable to wear shoes.

③ Stability of Adhesion and Fixability after Exercise

[1]: 90% or more of the applied pressure-sensitive adhesive showing no peel, with the taping function on the ankle continuing sufficiently;

[2]: 50% or more and less than 90% showing no peel, with partial loosening but maintaining the taping function;

[3]: Less than 50% showing no peel, with showing loosening and loss of the taping function.

TABLE 1

| | Evaluation Standard | Example 1 (Number of Persons) | Example 2 (Number of Persons) | Comparative Example 1 (Number of Persons) |
|---|---|---|---|---|
| Operability of taping | 1 | 20 | 20 | 0 |
| | 2 | 0 | 0 | 9 |
| | 3 | 0 | 0 | 11 |
| Conditions immediately after taping | 1 | 18 | 17 | 0 |
| | 2 | 2 | 3 | 2 |
| | 3 | 0 | 0 | 15 |
| | 4 | 0 | 0 | 3 |
| Stability of adhesion and fixability after exercise | 1 | 19 | 18 | 17 |
| | 2 | 1 | 2 | 2 |
| | 3 | 0 | 0 | 0 |

TABLE 2

|  | Evaluation Standard | Example 3 (Number of Persons) | Example 4 (Number of Persons) |
|---|---|---|---|
| Operability of taping | 1 | 20 | 13 |
|  | 2 | 0 | 7 |
|  | 3 | 0 | 0 |
| Conditions immediately after taping | 1 | 17 | 18 |
|  | 2 | 3 | 2 |
|  | 3 | 0 | 0 |
|  | 4 | 0 | 0 |
| Stability of adhesion and fixability after exercise | 1 | 19 | 17 |
|  | 2 | 1 | 3 |
|  | 3 | 0 | 0 |

The results shown in Tables 1 and 2 indicate that taping using the pressure-sensitive adhesive components for an ankle in Examples 1 to 4 by the method described in Examples 1 to 4 resulted in best evaluations by 13 persons or more out of the 20 person in all the evaluations of "Operability of taping", "Conditions immediately after taping", and "Stability of adhesion and fixability after exercise". That is, the pressure sensitive adhesive components for an ankle of the present invention are good in the feeling of wearing and operability and exhibit satisfactory taping function. Furthermore, it revealed that the pressure sensitive adhesive components for an ankle of the present invention have waterproof property On the other hand, Comparative Example 1 in which taping was performed by the conventional method indicated that the taping took a long time and many parsons complained for discomfort in the feeling of wearing the taping.

As described above in detail, use of the pressure-sensitive adhesive component for an ankle of the present invention enables a person having no expert knowledge on taping to perform readily and in a short time appropriate taping only by following the order indicated, for example, on the release liner. Since everybody can perform taping with ease, the present invention is very useful for preventing recurrence of sprained ankle that would otherwise tend to become chronic and also preventing serious physical damages.

The pressure-sensitive adhesive component for an ankle of the present invention enables sufficient fixing of an ankle joint and the like and assures continued fixability, so that they are useful for various kinds of athletes including walkers, joggers, hikers, climbers and so forth a well as rehabilitation trainees for the functional recovery of foot joints and the like. Furthermore, use of the pressure-sensitive adhesive components for an ankle of the present invention causes no thickening upon application and makes users to feel no inconvenience in daily life, allowing users to wear shoes, also allowing wearing athletes' shoes.

According to the taping method of the present invention, taping can be performed by placing the heel sole on the bottom portion of the H-shaped pressure-sensitive adhesive component or the like and loading the body weight thereon, so that there is no need to hold the pressure-sensitive adhesive component by one hand, thus allowing free use of hands, so that taping can be performed with free hands, thus assuring effective taping effects. Furthermore, according to the taping method of the present invention, taping can be performed in a state close to the state of that ankle joint or the like upon which a load is imposed when exercising, so that an effective taping effect tends to be shown easy.

According to the taping method of the present invention, neither local circulation disturbance nor nervous disturbance will occur due to over winding since no spiral winding around the ankle is involved.

The present invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which claims within the meaning and range of equivalency of the claims are therefore intended to b embraced therein.

The invention claimed is:

1. A pressure-sensitive adhesive component for an ankle, comprising an H-shaped pressure-sensitive adhesive component comprising:
    a substrate that is an elastic knitted fabric;
    a bottom portion sized and adapted to fit under a heel of a user and that allows an end of the heel to run off;
    a first tape-shaped body provided on the bottom portion; and
    a second tape-shaped body provided on the bottom portion,
    wherein a cut is provided between the first and second tape-shaped bodies running in a longitudinal direction with respect to the first and second tape-shaped bodies from edges of the first and second tape-shaped bodies, the first tape-shaped body including a first front tape body and a first rear tape body, where front and rear designate directions toward the toes and the heel, respectively, and the second tape-shaped body including a second front tape body and a second rear tape body, and
    wherein a first ratio of a width of the first front tape body to a width of the first rear tape body and a second ratio of a width of the second front tape body to a width of the second rear tape body are independently within the range of 5:5 to 5:3.

2. The pressure-sensitive adhesive component for an ankle as claimed in claim 1,
    wherein one edge of the bottom portion is concave, the one edge of the bottom portion is the edge on the side of the first and second rear tape bodies.

3. The pressure-sensitive adhesive component for an ankle as claimed in claim 2, wherein the H-shaped pressure-sensitive adhesive component has a length of 300 mm to 600 mm and the first and second tape-shaped bodies independently have a width of 50 mm to 150 mm.

4. The pressure-sensitive adhesive component for an ankle as claimed in claim 1,
    wherein the pressure-sensitive adhesive component is a modified H-shaped pressure-sensitive adhesive component, and
    wherein the first and second rear tape bodies have lengths shorter than those of the first and second front tape bodies.

5. The pressure-sensitive adhesive component for an ankle as claimed in claim 4,
    wherein the pressure-sensitive adhesive component has a length from an edge of the first front tape body to an end of the second front tape body of 400 mm to 650 mm, and
    wherein the first and second tape-shaped body independently have a width of 50 mm to 150 mm.

6. The pressure-sensitive adhesive component for an ankle as claimed in claim 4, wherein the first and second front tape bodies independently have a length of 200 mm to 270 mm.

7. The pressure-sensitive adhesive component for an ankle as claimed in claim 4, the first and second rear tape bodies independently have a length of 80 mm to 150 mm.

8. The pressure-sensitive adhesive component for an ankle as claimed in claim 1, wherein head portions of the first rear tape body, the first front tape body, the second rear tape body, and the second front tape body are each tongue-shaped.

9. The pressure-sensitive adhesive component for an ankle as claimed in claim 1, wherein a pressure-sensitive adhesive layer of the H-shaped pressure-sensitive adhesive component is covered with a release liner that is provided with a back slit at several positions.

10. The pressure-sensitive adhesive component for an ankle as claimed in claim 9, wherein the release liner that covers the pressure-sensitive adhesive layer and is separated by a back slit has indicated thereon a character or an image thereon.

11. A pressure-sensitive adhesive component for an ankle, comprising an integrally formed H-shaped pressure-sensitive component comprising:
- a bottom portion sized and adapted to fit under a heel of a user that allows an end of the heel to run off;
- a first tape-shaped body provided on the bottom portion and integrally formed therewith; and
- a second tape-shaped body provided on the bottom portion and integrally formed therewith;
- wherein a cut is provided in the integrally formed component between the first and second tape-shaped bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and
- wherein a first ratio of a width of the first front tape body to a width of the first rear tape body and a second ratio of a width of the second front tape body to a width of the second rear tape body are independently within the range of 5:5 to 5:3,
- wherein a pressure-sensitive adhesive layer of the H-shaped pressure-sensitive adhesive component is covered with a release liner that is provided with a back slit at several positions,
- wherein the release liner that covers the pressure-sensitive adhesive layer and is separated by a back slit has indicated thereon a character or an image thereon, and
- wherein one can recognize an order from the character or image on the release liner separated by the back slit.

12. A pressure-sensitive adhesive component for an ankle, comprising an integrally formed H-shaped pressure-sensitive component comprising:
- a bottom portion sized and adapted to fit under a heel of a user that allows an end of the heel to run off;
- a first tape-shaped body provided on the bottom portion and integrally formed therewith, and
- a second tape-shaped body provided on the bottom portion and integrally formed therewith,
- wherein a cut is provided in the integrally formed component between the first and second tape-shaped bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and
- wherein a first ratio of width of the first front tape body to a width of the first rear tape body and a second ratio of a width of the second front tape body to a width of the second rear tape body are independently within the range of 5:5 to 5:3,
- wherein the pressure-sensitive adhesive component includes a substrate made of one material selected from the group consisting of a high twist fabric and an elastic knitted fabric.

13. A pressure-sensitive adhesive component for an ankle, comprising an integrally formed H-shaped pressure-sensitive component comprising:
- a substrate that is an elastic knitted fabric;
- a bottom portion sized and adapted to fit under a heel of a user that allows an end of the heel to run off;
- a first tape-shaped body provided on the bottom portion and integrally formed therewith, and
- a second tape-shaped body provided on the bottom portion and integrally formed therewith,
- wherein a cut is provided in the integrally formed component between the first and second tape-shaped bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and
- wherein a first ratio of width of the first front tape body to a width of the first rear tape body and a second ratio of a width of the second front tape body to a width of the second rear tape body are independently within the range of 5:5 to 5:3,
- wherein the pressure-sensitive adhesive component includes a pressure-sensitive adhesive layer that is formed from one material selected from the group consisting of an acrylic pressure-sensitive adhesive and a gel pressure-sensitive adhesive.

14. A pressure-sensitive adhesive component for an ankle, comprising an integrally formed H-shaped pressure-sensitive component comprising:
- a substrate that is an elastic knitted fabric;
- a bottom portion sized and adapted to fit under a heel of a user that allows an end of the heel to run off;
- a first tape-shaped body provided on the bottom portion and integrally formed therewith, and
- a second tape-shaped body provided on the bottom portion and integrally formed therewith,
- wherein a cut is provided in the integrally formed component between the first and second tape-shaped bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and
- wherein a first ratio of width of the first front tape body to a width of the first rear tape body and a second ratio of a width of the second front tape body to a width of the second rear tape body are independently within the range of 5:5 to 5:3,
- wherein the pressure-sensitive adhesive component includes a support and a pressure-sensitive adhesive layer, and
- wherein the total of a thickness of the support and a thickness of the pressure-sensitive adhesive layer is 300 μm to 1,100 μm, and wherein the pressure-sensitive adhesive component consisting of a support and a pressure-sensitive adhesive layer has an elongation of 110% or less.

15. A pressure-sensitive adhesive component for an ankle, comprising an integrally formed H-shaped pressure-sensitive component comprising:
   a substrate that is an elastic knitted fabric;
   a bottom portion sized and adapted to fit under a heel of a user that allows an end of the heel to run off;
   a first tape-shaped body provided on the bottom portion and integrally formed therewith, and
   a second tape-shaped body provided on the bottom portion and integrally formed therewith,
   wherein a cut is provided in the integrally formed component between the first and second tape-shaped bodies running in a longitudinal direction with respect to the first and second tape-shaped bodies from edges of the first and second tape-shaped bodies, the first tape-shaped body including a first front tape body and a first rear tape body, and the second tape-shaped body including a second front tape body and a second rear tape body, and
   wherein a first ratio of width of the first front tape body to a width of the first rear tape body and a second ratio of a width of the second front tape body to a width of the second rear tape body are independently within the range of 5:5 to 5:3,
   further comprising an auxiliary pressure-sensitive adhesive component in a rectangular form having a shorter side and a longer side and a curved corner, as an independent element.

16. The pressure-sensitive adhesive component for an ankle as claimed in claim 15, wherein the auxiliary pressure-sensitive adhesive component includes a pressure-sensitive adhesive layer having thereon a release liner, the release liner is separated by a back split at two positions.

17. The pressure-sensitive adhesive component for an ankle as claimed in claim 16, wherein the pressure-sensitive adhesive component has a shorter side of 50 mm to 100 mm, a longer side of 100 mm to 350 mm.

18. A taping method of performing taping an ankle joint by using an H-shaped pressure-sensitive adhesive component, comprising:
   removing a release liner on a bottom portion, said bottom portion having a concave edge and being sized and adapted to fit under a heel of a user and that allows an end of the heel to run off;
   placing a heel such that an edge of the heel is in line with a concave edge of the bottom portion;
   removing a release liner on a front tape portion to be applied to an outer side of the ankle portion and applying the front tape portion with holding a head portion of a front tape body while expanding the front tape portion so as to cover a medial malleolus of the ankle portion from a heel toward a knee joint;
   removing a release liner on a front tape head portion and applying the front tape head portion;
   removing a release liner on a front tape portion to be applied to an inner side of the ankle portion and applying the front tape portion while drawing up the front tape portion just above and expanding;
   removing a release liner on a front tape head portion and applying the front tape head portion;
   removing a release liner on a rear tape portion positioned on an outer side of the ankle portion and applying the rear tape portion by holding a head portion of a rear tape body so as to pass along the back side of the ankle portion and cover over the medial malleolus while expanding the rear tape portion;
   removing a release liner of a rear tape head portion and applying the rear tape head portion;
   removing a release liner on a rear tape portion positioned on the inner side of the ankle portion and applying the rear tape portion by holding a head portion of a rear tape body and while expanding the rear tape portion so as to pass along the back side of the ankle portion and cover over the lateral malleolus; and
   removing a release liner of a rear tape head portion and applying the rear tape head portion.

19. The taping method as claimed in claim 18, wherein one edge of the auxiliary pressure-sensitive adhesive is applied onto the rear tape portion so as to cover the lateral malleolus of the ankle portion in an overlapping manner and then the other edge of the auxiliary pressure-sensitive adhesive component is applied to onto the other rear tape portion so as to cover the medial malleolus of the ankle portion in an overlapping manner.

20. A taping method by using a modified H-shaped pressure-sensitive adhesive component, comprising:
   removing a release liner of a bottom portion and placing a heel on the bottom portion wherein the bottom portion allows an end of the heel to run off and such that a rear tape body covers a surface of malleolus when elevated vertically;
   removing a release liner of one of the rear tape bodies and applying the rear tape body by holding a head portion of the rear tape body to lift the rear tape body vertically while expanding the rear tape body so as to cover the lateral malleolus of the ankle portion;
   removing a release liner of the other rear tape body to be applied to an inner side of the ankle portion and applying the rear tape body while lifting the rear tape body vertically to expand the rear tape body so as to cover an inner side of the ankle portion; removing a release liner of one of the front tape bodies positioned on an outer side of the ankle portion and applying the front tape body while holding a head portion of the front tape body to expand the front tape body so as to pass along an entire loop from above the dorsum of foot and the ankle portion and cover over the lateral malleolus and further pass Achilles' tendon on the back side of the ankle to the lateral malleolus; and
   removing a release liner of the other front tape body positioned on the inner side of the ankle portion and applying the front tape body while holding a head portion of the front tape body to expand the front tape body so as to pass along an entire loop including crossing at the ankle portion above the dorsum of foot to cover over the lateral malleolus, passing the Achilles' tendon to reach the medial malleolus.

* * * * *